United States Patent
Tizhoosh et al.

(10) Patent No.: US 11,615,895 B2
(45) Date of Patent: *Mar. 28, 2023

(54) SYSTEMS AND METHODS FOR AUTOMATICALLY MANAGING IMAGE DATA

(71) Applicant: Huron Technologies International Inc., St. Jacobs (CA)

(72) Inventors: Hamid Reza Tizhoosh, St. Jacobs (CA); Patrick Myles, St. Jacobs (CA); Savvas Damaskinos, St. Jacobs (CA)

(73) Assignee: Huron Technologies International Inc., St. Jacobs (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/901,098

(22) Filed: Sep. 1, 2022

(65) Prior Publication Data

US 2022/0415522 A1    Dec. 29, 2022

Related U.S. Application Data

(63) Continuation of application No. 17/465,297, filed on Sep. 2, 2021, now Pat. No. 11,476,005.

(Continued)

(51) Int. Cl.
*G16H 50/70* (2018.01)
*G06K 9/62* (2022.01)
(Continued)

(52) U.S. Cl.
CPC ............ *G16H 50/70* (2018.01); *G06F 16/51* (2019.01); *G06F 16/532* (2019.01); *G06K 9/6215* (2013.01); *G16H 30/20* (2018.01)

(58) Field of Classification Search
CPC ........ G16H 30/20; G16H 50/20; G16H 50/70; G06V 10/759; G06V 2201/03;
(Continued)

(56) References Cited

U.S. PATENT DOCUMENTS 8,077,959 B2   12/2011   Dekel et al.
9,962,125 B2    5/2018   Hwang
(Continued)

FOREIGN PATENT DOCUMENTS

WO    2020093152 A1    5/2020
WO    2020190518 A1    9/2020

OTHER PUBLICATIONS

Krupinski, Elizabeth A., et al. "Compressing pathology whole-slide images using a human and model observer evaluation." Journal of pathology informatics 3 (2012).
(Continued)

*Primary Examiner* — Manuchehr Rahmjoo
(74) *Attorney, Agent, or Firm* — Bereskin & Parr LLP/S.E.N.C.R.L., s.r.l.

(57) ABSTRACT

Computer-implemented methods and systems are provided for curating medical images for a medical image database. An example method for curating involves operating a processor to obtain a query medical image, assign the query medical image to an initial set of related images, and generate a similarity indicator for each image of the initial set. The similarity indicator is representative of a measure of similarity between image data of that image and the initial set. The processor is operable to define an intermediate set from the initial set based on the similarity indicators; and generate a relevancy indicator for each image of the intermediate set. The relevancy indicator is representative of a measure of the relevancy between relevance of the image and the intermediate set. The processor is operable to define a curated set of images from the intermediate set based on the relevancy indicators.

24 Claims, 18 Drawing Sheets

Related U.S. Application Data

(60) Provisional application No. 63/074,115, filed on Sep. 3, 2020.

(51) Int. Cl.
    *G06F 16/532*        (2019.01)
    *G16H 30/20*         (2018.01)
    *G06F 16/51*         (2019.01)

(58) Field of Classification Search
    CPC ...... G06N 3/0454; G06N 3/08; G06K 9/6215; G06F 16/24578; G06F 16/532; G06F 16/538; G06F 16/55; G06F 16/583; G06F 16/5854
    See application file for complete search history.

(56) References Cited

U.S. PATENT DOCUMENTS

| | | | |
|---|---|---|---|
| 10,404,894 | B2 | 9/2019 | Hwang |
| 10,628,736 | B2 | 4/2020 | Tizhoosh |
| 11,042,772 | B2 | 6/2021 | Tizhoosh et al. |
| 2003/0163031 | A1 | 8/2003 | Madden et al. |
| 2015/0356733 | A1 | 12/2015 | Soldea et al. |
| 2021/0019342 | A1* | 1/2021 | Peng ............... G16H 30/20 |

OTHER PUBLICATIONS

Yagi, Yukako, and John R. Gilbertson. "Digital imaging in pathology: the case for standardization." (2005): 109-116.

Sanchez, Victor, et al. "Fast lossless compression of whole slide pathology images using HEVC in-tra-prediction." 2016 IEEE International Conference on Acoustics, Speech and Signal Processing (ICASSP). IEEE, 2016.

Hernández-Cabronero, Miguel, et al. "Transform optimization for the lossy coding of pathology whole-slide images." 2016 Data Compression Conference (DCC). IEEE, 2016.

Huisman, André, et al. "Creation of a fully digital pathology slide archive by high-volume tissue slide scanning." Human pathology 41.5 (2010): 751-757.

Erickson, Bradley J. "Irreversible compression of medical images." Journal of Digital Imaging 15.1 (2002): 5-14.

Sharma, Anurag, Pinky Bautista, and Yukako Yagi. "Balancing image quality and compression factor for special stains whole slide images." Analytical Cellular Pathology 35.2 (2012): 101-106.

Farahani, Navid, Anil V. Parwani, and Liron Pantanowitz. "Whole slide imaging in pathology: advantages, limitations, and emerging perspectives." Pathol Lab Med Int 7 (2015): 23-33.

Pantanowitz, Liron. "Digital images and the future of digital pathology." Journal of pathology informatics 1 (2010).

Park, Seung, Liron Pantanowitz, and Anil Vasdev Parwani. "Digital imaging in pathology." Clinics in laboratory medicine 32.4 (2012): 557-584.

Ghaznavi, Farzad, et al. "Digital imaging in pathology: whole-slide imaging and beyond." Annual Review of Pathology: Mechanisms of Disease 8 (2013): 331-359.

Stathonikos, Nikolas, et al. "Being fully digital: Perspective of a Dutch academic pathology lab." Histopathology (2019).

Tizhoosh, Hamid Reza, and Liron Pantanowitz. "Artificial intelligence and digital pathology: Challenges and opportunities." Journal of pathology informatics 9 (2018).

Kumar, Meghana Dinesh, et al. "A comparative study of cnn, bovw and lbp for classification of histopathological images." 2017 IEEE Symposium Series on Computational Intelligence (SSCI). IEEE, 2017.

Kalra, S., et al. "Yottixel—An Image Search Engine for Large Archives of Histopathology Whole Slide Images." arXiv preprint arXiv:1911.08748 (2019).

Babaie, Morteza, and Hamid R. Tizhoosh. "Deep Features for Tissue-Fold Detection in Histopatholo-gy Images." arXiv preprint arXiv:1903.07011 (2019).

Chenni, Wafa, et al. "Patch Clustering for Representation of Histopathology Images." arXiv preprint arXiv: 1903.07013 (2019).

Bera, Kaustav, et al. "Artificial intelligence in digital pathology—new tools for diagnosis and precision oncology." Nature Reviews Clinical Oncology 16.11 (2019): 703-715.

Bettie, Peter, "Written Opinion of the International Search Authority" and "International Search Report", dated Dec. 1, 2021, International Application No. PCT/CA2021/051215, Canadian Intellectual Property Office, 13 pages.

Selvarani, A., "Medical Image Retrieval by Combining Low Level Features and DICOM Features", International Conference on Computational Intelligence and Multimedia Applications 2007, Dec. 15, 2007 (Dec. 15, 2007), pp. 587-591, ISBN 0-7695-3050-8 [online].

Lascoste, C., "Medical-Image Retrieval Based on Knowledge-Assisted Text and Image Indexing", IEEE Transactions on Circuits and Systems for Video Technology, Jul. 2, 2007 (Jul. 2, 2007), vol. 17, No. 7, pp. 889-900, [online].

\* cited by examiner

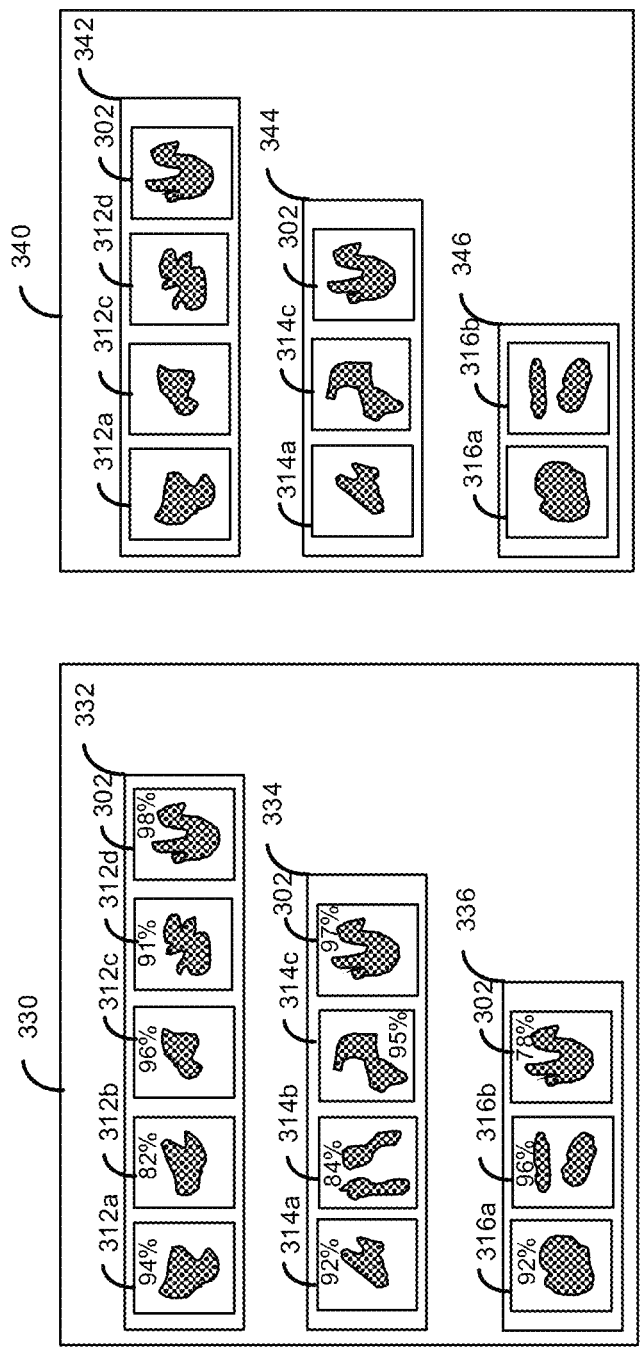

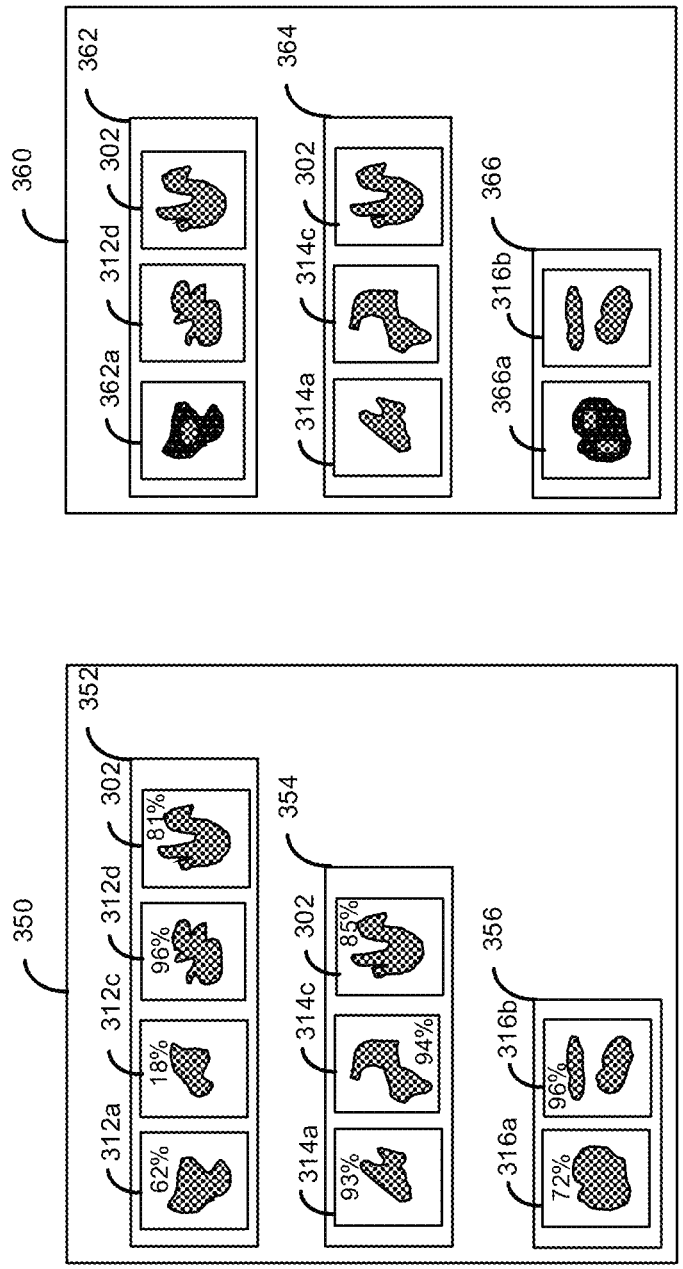

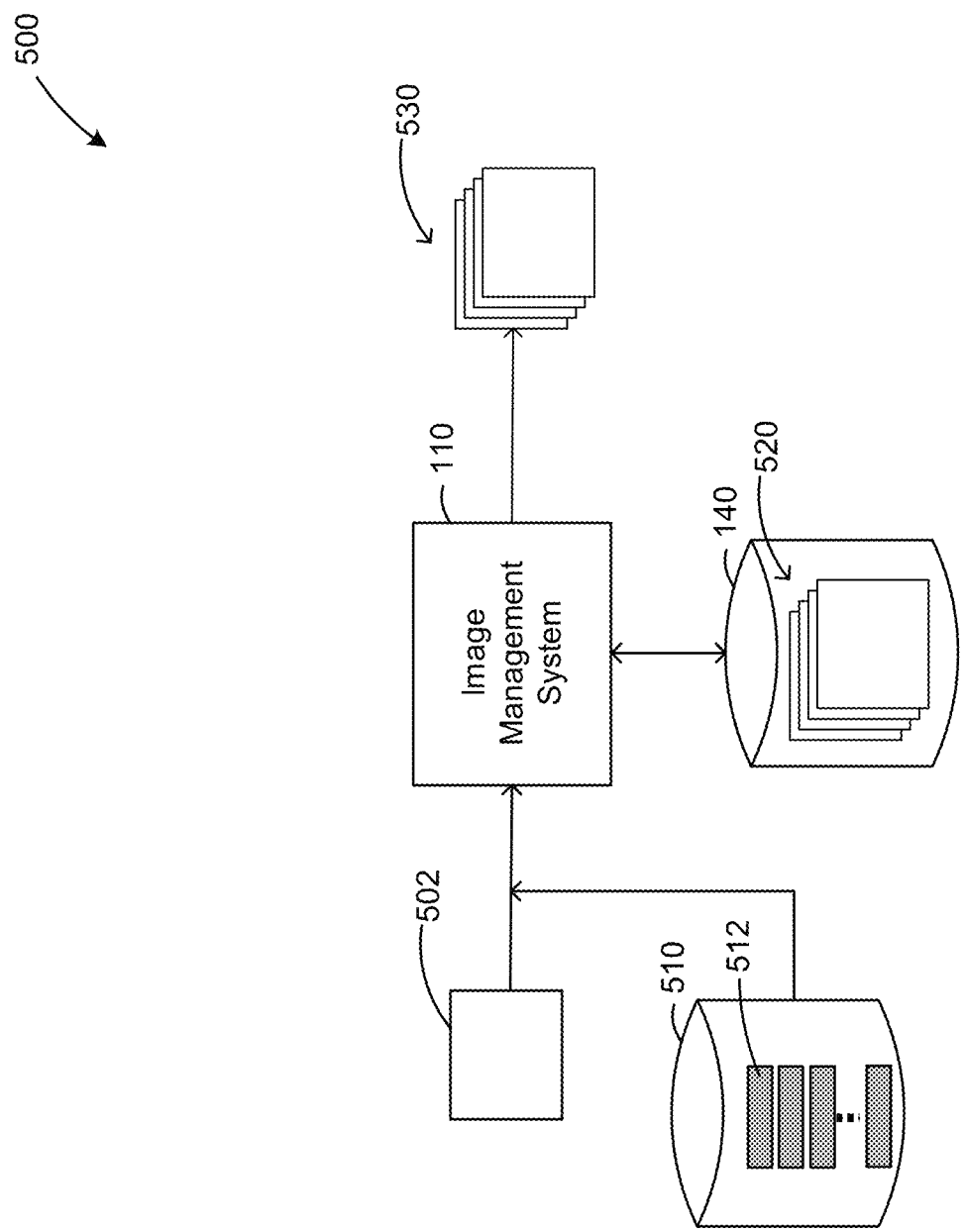

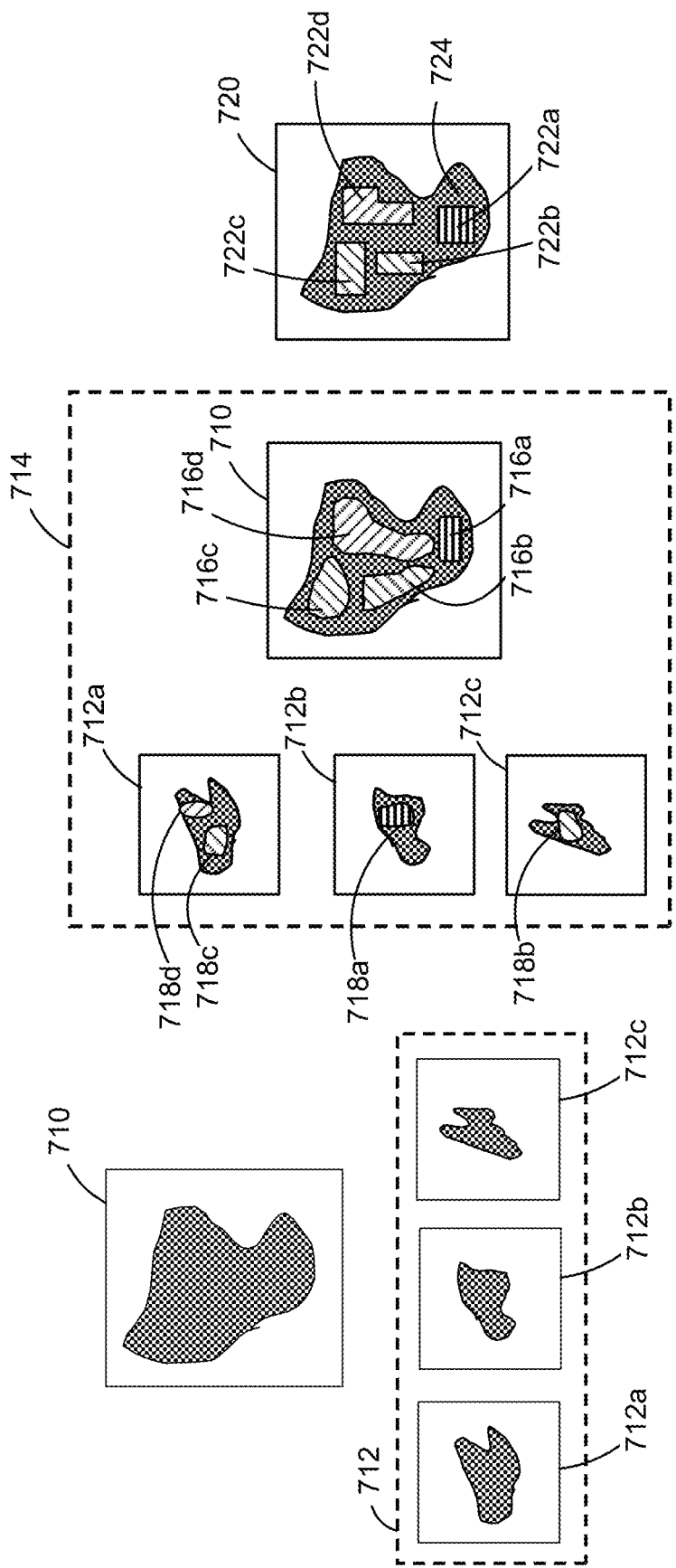

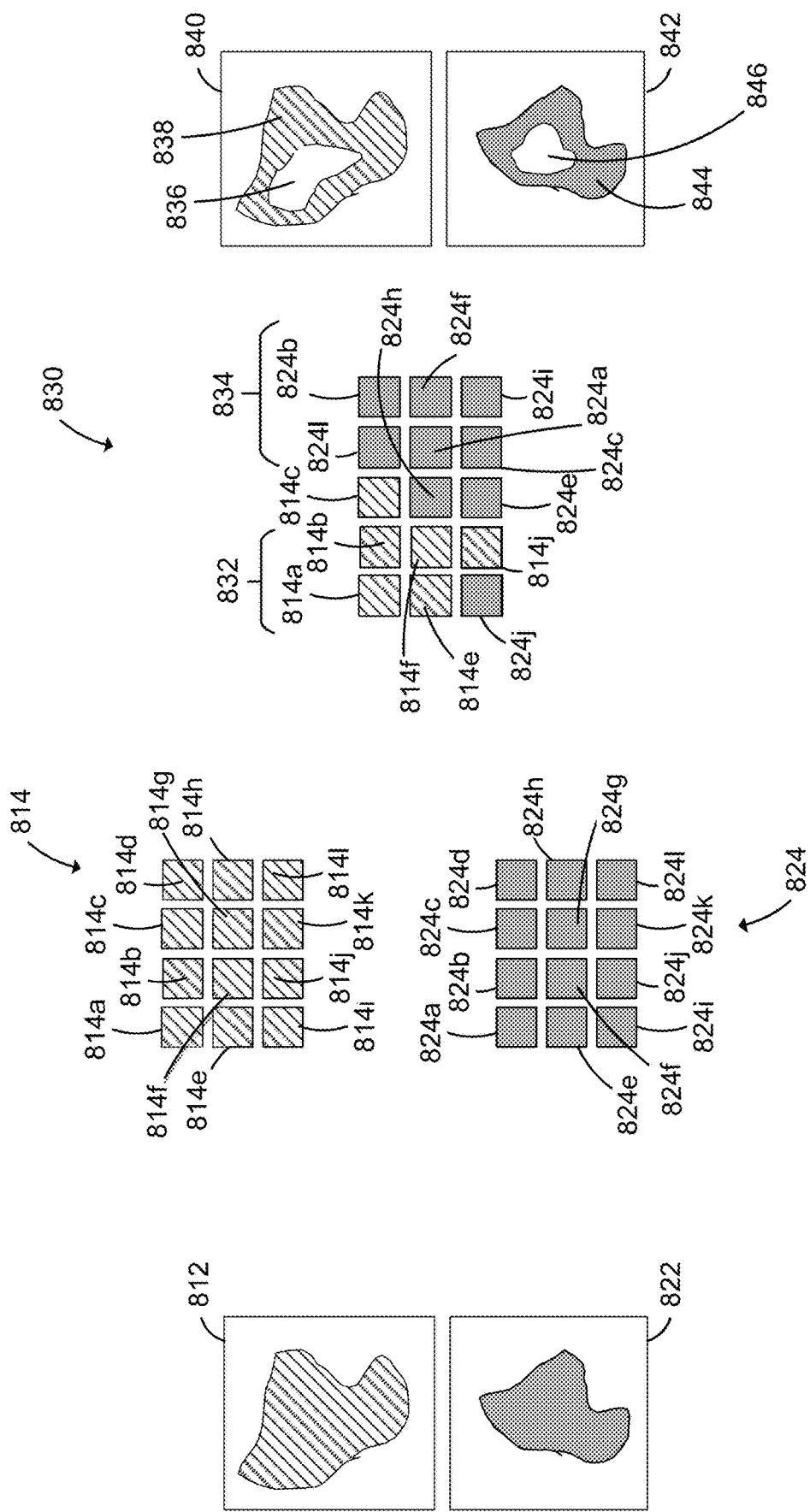

SYSTEMS AND METHODS FOR AUTOMATICALLY MANAGING IMAGE DATA

CROSS-REFERENCE TO RELATED PATENT APPLICATIONS

This application is a continuation of U.S. patent application Ser. No. 17/465,297 filed on Sep. 2, 2021, which claims the benefit of U.S. Provisional Patent Application No. 63/074,115, filed on Sep. 3, 2020. The complete disclosure of each of U.S. patent application Ser. No. 17/465,297 and Provisional Patent Application No. 63/074,115 is incorporated herein by reference for all purposes.

FIELD

The described embodiments relate to systems and methods of managing image data and in particular, systems and methods of curating medical image data.

BACKGROUND

Digital images and videos are increasingly common forms of media. For example, the practice of pathology is undergoing a digital transformation, moving from a microscope-based workflow to digital pathology workflows. That means, instead of looking at biopsy samples under a light microscope, pathologists and researchers are increasingly viewing, analyzing and sharing digital images captured by modern scanners. This digital transformation is being driven in part by technological advancement and also by the desire to provide faster and more accurate diagnosis and to address the severe shortage of pathologists, particularly subspecialty experts.

Digital pathology involves examination of digital images of tissue specimens. Diagnosis of digital images requires high resolution images, which typically entails large amounts of data. Data storage, particularly high performance data storage allowing for fast access, can be expensive. As more digital content is generated, the storage of digital content can be an obstacle to the adoption of digital pathology. In addition, the usefulness of that digital content largely depends on its management.

Some existing management practices involve image compression. Such methods can be limited because diagnosis generally requires lossless image compression. In addition, digital content from old cases can be deleted to make room for new cases. However, retention of previously diagnosed cases can be desirable as they can be used as a knowledge base for future case studies, training, and diagnosis.

SUMMARY

The various embodiments described herein generally relate to methods (and associated systems configured to implement the methods) of curating medical images for a medical image database.

An example method can involve operating a processor to, obtain one or more query medical images, each query medical image having an identifier that is representative of image data of that query medical image; and assign each query medical image to at least one initial set of related medical images from the medical image database based on the identifier for that query medical image. The initial set can include the query medical image and at least one supplemental medical image. The method can also involve operating the processor to, for each initial set of related medical images, generate a similarity indicator for each medical image of the initial set, and define an intermediate set of medical images from the initial set based on the similarity indicator of each medical image of the initial set. The similarity indicator can be representative of a measure of similarity between image data of that medical image and image data of the initial set. The method can also involve operating the processor to, for each intermediate set of related medical images, generate a relevancy indicator for each medical image of the intermediate set, and define a curated set of medical images for storage in the medical image database from the medical images in the intermediate set based on the relevancy indicator of each medical image. The relevancy indicator can be representative of a measure of the relevancy between the medical image and the intermediate set. The relevancy can be representative of correlations between a plurality of relevance parameters associated with the medical image and the intermediate set.

In some embodiments, the curated set of medical images can exclude the query medical image.

In some embodiments, the curated set of medical images can include the query medical image.

In some embodiments, the curated set of medical images can exclude one or more supplemental medical images.

In some embodiments, the method can involve for each medical image of the intermediate set, normalizing a measure of relevancy between relevance parameters of the query medical image and relevance parameters of medical images of the intermediate set of medical images.

In some embodiments, the method can involve determining whether the relevancy indicator for a medical image exceeds a first relevancy threshold; and in response to determining that the relevancy indicator of the medical image does not exceed the first relevancy threshold, excluding the medical image from the curated set of medical images, otherwise including the medical image to the curated set of medical images.

In some embodiments, the method can involve storing a version of a medical image in the curated set of medical images.

In some embodiments, the method can involve determining whether the relevancy indicator of a medical image exceeds a second relevancy threshold; and in response to determining that the relevancy indicator of the medical image does not exceed the second relevancy threshold, storing a version of the medical image in the curated set of medical images, otherwise storing the medical image in the curated set of medical images.

In some embodiments, the method can involve, for each of the one or more versions of a medical image: identifying one or more portions of image data of the medical image that is analogous to image data of another medical image in the curated set of medical images; storing the one or more portions of image data of the medical image that is analogous to image data of the other medical image in the curated set; and storing a remaining portion of image data of the version of the medical image that is not analogous to other medical images in the curated set of medical images.

In some embodiments, the remaining portion of image data can include low resolution image data.

In some embodiments, the method can involve storing an association between the analogous image data of the medical image and the other medical image in the curated set.

In some embodiments, the method can involve storing higher resolution image data of the one or more portions of analogous image data from the version of the medical image.

In some embodiments, the one or more portions of image data of the medical images in the curated set can be sorted in order of similarity to the version of the medical image.

In some embodiments, the one or more portions of image data of the medical images in the curated set can be sorted in order of decreasing similarity to the version of the medical image.

In some embodiments, the method can involve determining a measure of similarity between the identifier of the version of the medical image and identifiers for the other medical images in the curated set of medical images.

In some embodiments, the method can involve for each intermediate set: receiving the plurality of relevance parameters for the medical images of the intermediate set; generating a plurality of membership values by applying a set of input membership functions to the relevance parameters for each medical image of the intermediate set; generating an output membership function for each medical image of the intermediate set by applying a set of rules to the plurality of membership values for that medical image of the intermediate set to quantify the relevancy of that medical image of the intermediate set; and generating the relevancy indicator for each of the medical images of the intermediate set by quantifying the output membership function for that medical image.

In some embodiments, the method can involve generating the identifier for the query medical image.

In some embodiments, the method can involve storing the identifier for the query medical image in the medical image database.

In some embodiments, the method can involve storing the relevancy indicator for the query medical image in the medical image database.

In some embodiments, the method can involve for each supplemental medical image of the initial set, normalizing a measure of similarity between the identifier of the query medical image and the identifier of the supplemental medical image.

In some embodiments, the method can involve determining whether the similarity indicator for that medical image exceeds a similarity threshold; and in response to determining that the similarity indicator for that medical image exceeds the similarity threshold, assigning that medical image to the intermediate set.

In some embodiments, the method can involve temporarily storing the query medical images.

In some embodiments, the method can involve deleting the query medical images.

In some embodiments, the method can involve storing the similarity indicator for the query medical image in the medical image database.

In some embodiments, the method can involve obtaining the one or more query medical images from an imaging device; and for each query medical image, generating the identifier that is representative of image data of that query medical image.

In another broad aspect, a system for curating medical images for a medical image database is disclosed herein. The system can include a communication component and a processor in communication with the communication component. The communication component can provide access to the one or more images via a network. The processor can be operable to obtain one or more query medical images, each query medical image having an identifier that is representative of image data of that query medical image; and assign each query medical image to at least one initial set of related medical images from the medical image database based on the identifier for that query medical image. The initial set can include the query medical image and at least one supplemental medical image. The processor can be operable to, for each initial set of related medical images, generate a similarity indicator for each medical image of the initial set, and define an intermediate set of medical images from the initial set based on the similarity indicator of each medical image of the initial set. The similarity indicator can represent a measure of similarity between image data of that medical image and image data of the initial set. The processor can be operable to, for each intermediate set of related medical images, generate a relevancy indicator for each medical image of the intermediate set, and define a curated set of medical images for storage in the medical image database from the medical images in the intermediate set based on the relevancy indicator of each medical image. The relevancy indicator can be representative of a measure of the relevancy between the medical image and the intermediate set. The relevancy can be representative of correlations between a plurality of relevance parameters associated with the medical image and the intermediate set.

In some embodiments, the curated set of medical images can exclude the query medical image.

In some embodiments, the curated set of medical images can include the query medical image.

In some embodiments, the curated set of medical images can exclude one or more supplemental medical images.

In some embodiments, the processor can be operable to, for each medical image of the intermediate set, normalize a measure of relevancy between relevance parameters of the query medical image and relevance parameters of medical images of the intermediate set of medical images.

In some embodiments, the processor can be operable to, determine whether the relevancy indicator for a medical image exceeds a first relevancy threshold; and in response to determining that the relevancy indicator of the medical image does not exceed the first relevancy threshold, exclude the medical image from the curated set of medical images, otherwise assign the medical image to the curated set of medical images.

In some embodiments, the processor can be operable to store a version of a medical image in the curated set of medical images.

In some embodiments, the processor can be operable to, determine whether the relevancy indicator of a medical image exceeds a second relevancy threshold; and in response to determining that the relevancy indicator of the medical image does not exceed the second relevancy threshold, store a version of a medical image in the curated set of medical images, otherwise store the medical image in the curated set of medical images.

In some embodiments, the processor can be operable to, for each of the one or more versions of a medical images, identify one or more portions of image data of the version of the medical image that is analogous to image data of the another medical image in the curated set of medical images; and store the one or more portions of image data of the medical image that is analogous to image data of the other medical image in the curated set, and store a remaining portion of image data of the version of the medical image that is not analogous to other medical images in the curated set of medical images.

In some embodiments, the remaining portion of image data can include low resolution image data.

In some embodiments, the processor can be operable to store an association between the analogous image data of the version of the medical image and the other medical image in the curated set.

In some embodiments, the processor can be operable to store higher resolution image data of the one or more portions of analogous image data from the version of the medical image.

In some embodiments, the one or more portions of image data of the medical images in the curated set can be sorted in order of similarity to the version of the medical image.

In some embodiments, the one or more portions of image data of the medical images in the curated set can be sorted in order of decreasing similarity to the version of the medical image.

In some embodiments, the processor can be operable to determine a measure of similarity between the identifier of the version of the medical image and identifiers for the other medical images in the curated set of medical images.

In some embodiments, the processor can be operable to, for each intermediate set, receive the plurality of relevance parameters for each of the medical images of the intermediate set; generate a plurality of membership values by applying a set of input membership functions to the relevance parameters for each medical image of the intermediate set; generate an output membership function for each medical image of the intermediate set by applying a set of rules to the plurality of membership values for that medical image of the intermediate set to quantify the relevancy of that medical image of the intermediate set; and generate the relevancy indicator for each of the medical images of the intermediate set by quantifying the output membership function for that medical image.

In some embodiments, the processor can be operable to generate the identifier for the query medical image.

In some embodiments, the processor can be operable to store the identifier for the query medical image in the medical image database.

In some embodiments, the processor can be operable to store the relevancy indicator for the query medical image in the medical image database.

In some embodiments, the processor can be operable to, for each supplemental medical image of the initial set, normalize a measure of similarity between the identifier of the query medical image and the identifier of the supplemental medical image.

In some embodiments, the processor can be operable to, determine whether the similarity indicator for that medical image exceeds a similarity threshold; and in response to determining that the similarity indicator for that medical image exceeds the similarity threshold, assign that medical image to the intermediate set.

In some embodiments, the processor can be operable to temporarily store the query medical images.

In some embodiments, the processor can be operable to delete the query medical images.

In some embodiments, the processor can be operable to store the similarity indicator for the query medical image in the medical image database.

In some embodiments, the processor can be operable to, obtain the one or more query medical images from an imaging device; and for each query medical image, generate the identifier that is representative of image data of that query medical image.

In another broad aspect, a method of curating medical images for a medical image database is disclosed. The method can involve operating a processor to: obtain one or more query medical images, each query medical image having an identifier that is representative of image data of that query medical image; and assign each query medical image to at least one initial set of related medical images from the medical image database based on the identifier for that query medical image. The initial set can include the query medical image and at least one supplemental medical image. The method can also involve operating the processor to, for each initial set of related medical images, generate a relevancy indicator for each medical image of the initial set, and define a curated set of medical images for storage in the medical image database from the medical images in the initial set based on the relevancy indicator of each medical image. The relevancy indicator can be representative of a measure of the relevancy between the medical image and the initial set. The relevancy can be representative of correlations between a plurality of relevance parameters associated with the medical image and the initial set.

In some embodiments, the curated set of medical images can exclude the query medical image.

In some embodiments, the curated set of medical images can include the query medical image.

In some embodiments, the curated set of medical images can exclude one or more supplemental medical images.

In some embodiments, the method can involve for each medical image of the initial set, normalizing a measure of relevancy between relevance parameters of the query medical image and relevance parameters of medical images of the initial set of medical images.

In some embodiments, the method can involve determining whether the relevancy indicator for a medical image exceeds a first relevancy threshold; and in response to determining that the relevancy indicator of the medical image does not exceed the first relevancy threshold, excluding the medical image from the curated set of medical images, otherwise including the medical image to the curated set of medical images.

In some embodiments, the method can involve storing a version of a medical image in the curated set of medical images.

In some embodiments, the method can involve determining whether the relevancy indicator of a medical image exceeds a second relevancy threshold; and in response to determining that the relevancy indicator of the medical image does not exceed the second relevancy threshold, storing a version of the medical image in the curated set of medical images, otherwise storing the medical image in the curated set of medical images.

In some embodiments, the method can involve, for each of the one or more versions of a medical image: identifying one or more portions of image data of the version of the medical image that is analogous to image data of another medical image in the curated set of medical images; storing the one or more portions of image data of the medical image that is analogous to image data of the other medical image in the curated set; and storing a remaining portion of image data of the version of the medical image that is not analogous to other medical images in the curated set of medical images.

In some embodiments, the remaining portion of image data can include low resolution image data.

In some embodiments, the method can involve storing an association between the analogous image data of the medical image and the other medical image in the curated set.

In some embodiments, the method can involve storing higher resolution image data of the one or more portions of analogous image data from the version of the medical image.

In some embodiments, the one or more portions of image data of the medical images in the curated set can be sorted in order of similarity to the version of the medical image.

In some embodiments, the one or more portions of image data of the medical images in the curated set can be sorted in order of decreasing similarity to the version of the medical image.

In some embodiments, the method can involve determining a measure of similarity between the identifier of the version of the medical image and identifiers for the other medical images in the curated set of medical images.

In some embodiments, the method can involve, for each initial set: receiving the plurality of relevance parameters for the medical images of the initial set; generating a plurality of membership values by applying a set of input membership functions to the relevance parameters for each medical image of the initial set; generating an output membership function for each medical image of the initial set by applying a set of rules to the plurality of membership values for that medical image of the initial set to quantify the relevancy of that medical image of the initial set; and generating the relevancy indicator for each of the medical images of the initial set by quantifying the output membership function for that medical image.

In some embodiments, the method can involve generating the identifier for the query medical image.

In some embodiments, the method can involve storing the identifier for the query medical image in the medical image database.

In some embodiments, the method can involve storing the relevancy indicator for the query medical image in the medical image database.

In some embodiments, the method can involve temporarily storing the query medical images.

In some embodiments, the method can involve deleting the query medical images.

In some embodiments, the method can involve obtaining the one or more query medical images from an imaging device; and for each query medical image, generating the identifier that is representative of image data of that query medical image.

In another broad aspect, a system for curating medical images for a medical image database is disclosed herein. The system can include a communication component and a processor in communication with the communication component. The communication component can provide access to the one or more images via a network. The processor can be operable to obtain one or more query medical images, each query medical image having an identifier that is representative of image data of that query medical image; and assign each query medical image to at least one initial set of related medical images from the medical image database based on the identifier for that query medical image. The initial set can include the query medical image and at least one supplemental medical image. The processor can be operable to, for each initial set of related medical images, generate a relevancy indicator for each medical image of the initial set, and define a curated set of medical images for storage in the medical image database from the medical images in the initial set based on the relevancy indicator of each medical image. The relevancy indicator can be representative of a measure of the relevancy between the medical image and the initial set. The relevancy can be representative of correlations between a plurality of relevance parameters associated with the medical image and the initial set.

In some embodiments, the curated set of medical images can exclude the query medical image.

In some embodiments, the curated set of medical images can include the query medical image.

In some embodiments, the curated set of medical images can exclude one or more supplemental medical images.

In some embodiments, the processor can be operable to, for each medical image of the initial set, normalize a measure of relevancy between relevance parameters of the query medical image and relevance parameters of medical images of the initial set of medical images.

In some embodiments, the processor can be operable to, determine whether the relevancy indicator for a medical image exceeds a first relevancy threshold; and in response to determining that the relevancy indicator of the medical image does not exceed the first relevancy threshold, exclude the medical image from the curated set of medical images, otherwise assign the medical image to the curated set of medical images.

In some embodiments, the processor can be operable to, store a version of a medical image in the curated set of medical images.

In some embodiments, the processor can be operable to, determine whether the relevancy indicator of a medical image exceeds a second relevancy threshold; and in response to determining that the relevancy indicator of the medical image does not exceed the second relevancy threshold, store a version of a medical image in the curated set of medical images, otherwise store the medical image in the curated set of medical images.

In some embodiments, the processor can be operable to, for each of the one or more versions of a medical image: identify one or more portions of image data of the version of a medical image that is analogous to image data of another medical image in the curated set; store the one or more portions of image data of the medical image that is analogous to image data of the other medical image in the curated set; and store a remaining portion of image data of the version of the medical image that is not analogous to other medical images in the curated set of medical images.

In some embodiments, the remaining portion of image data can include low resolution image data.

In some embodiments, the processor can be operable to store an association between the analogous image data of the medical image and the other medical image in the curated set.

In some embodiments, the processor can be operable to store higher resolution image data of the one or more portions of analogous image data from the version of the medical image.

In some embodiments, the one or more portions of image data of the medical images in the curated set can be sorted in order of similarity to the version of the medical image.

In some embodiments, the one or more portions of image data of the medical images in the curated set can be sorted in order of decreasing similarity to the version of the medical image.

In some embodiments, the processor can be operable to determine a measure of similarity between the identifier of the version of the medical image and identifiers for other medical images in the curated set of medical images.

In some embodiments, the processor can be operable to, for each initial set: receive the plurality of relevance parameters for each of the medical images of the initial set; generate a plurality of membership values by applying a set of input membership functions to the relevance parameters for each medical image of the initial set; generate an output membership function for each medical image of the initial set by applying a set of rules to the plurality of membership values for that medical image of the initial set to quantify the relevancy of that medical image of the initial set; and generate the relevancy indicator for each of the medical images of the initial set by quantifying the output membership function for that medical image.

In some embodiments, the processor can be operable to generate the identifier for the query medical image.

In some embodiments, the processor can be operable to store the identifier for the query medical image in the medical image database.

In some embodiments, the processor can be operable to store the relevancy indicator for the query medical image in the medical image database.

In some embodiments, the processor can be operable to store the query medical images.

In some embodiments, the processor can be operable to delete the query medical images.

In some embodiments, the processor can be operable to, obtain the one or more query medical images from an imaging device; and for each query medical image, generate the identifier that is representative of image data of that query medical image.

In another broad aspect, a method of curating medical images for a medical image database is disclosed. The method can involve operating a processor to: obtain one or more query medical images and one or more supplementary medical images from the medical image database. The method can also involve operating the processor to: for each of the one or more query medical images, for each of the one or more supplementary medical images, identify one or more portions of image data of the query medical image that is analogous to image data of the supplementary medical image; store the one or more portions of image data of the query medical image that is analogous to image data of the supplementary medical image; and store a remaining portion of image data of the query medical image that is not analogous to the one or more supplementary medical images from the medical image database.

In some embodiments, the remaining portion of image data can include low resolution image data.

In some embodiments, the method can involve storing an association between the analogous image data of the supplementary medical image and the query medical image.

In some embodiments, the method can involve storing low resolution image data of the one or more portions of analogous image data from the query medical image.

In some embodiments, the one or more supplementary medical images can be stored in order of similarity to the query medical image.

In some embodiments, the one or more supplementary medical images can be stored in order of decreasing similarity to the query medical image.

In some embodiments, the method can involve determining a measure of similarity between an identifier of the query medical image and identifiers for the supplementary medical images to identify one or more portions of image data of the query medical image that is analogous to image data of one or more supplementary medical images.

In some embodiments, the method can involve for each query medical image, generating the identifier that is representative of image data of that query medical image; and for each supplementary medical image, generating the identifier that is representative of image data of that supplementary medical image.

In some embodiments, the method can involve obtaining the one or more query medical images from an imaging device.

In another broad aspect, a system for curating medical images is disclosed herein. The system can include a communication component and a processor in communication with the communication component. The communication component can provide access to the one or more images via a network. The processor can be operable to obtain one or more query medical images and one or more supplementary medical images from the medical image database. The processor can also be operable to: for each of the one or more query medical images, for each of the one or more supplementary medical images, identify one or more portions of image data of the query medical image that is analogous to image data of the supplementary medical image; store the one or more portions of image data of the query medical image that is analogous to image data of the supplementary medical image; and store a remaining portion of image data of the query medical image that is not analogous to the one or more supplementary medical images from the medical image database.

In some embodiments, the remaining portion of image data can include low resolution image data.

In some embodiments, the processor can be operable to store an association between the analogous image data of the supplementary medical image and the query medical image.

In some embodiments, the processor can be operable to store low resolution image data of the one or more portions of analogous image data from the version of the medical image.

In some embodiments, the one or more supplementary medical images can be stored in order of similarity to the query medical image.

In some embodiments, the one or more supplementary medical images can be stored in order of decreasing similarity to the query medical image.

In some embodiments, the processor can be operable to determine a measure of similarity between an identifier of the query medical image and identifiers for the supplementary medical images to identify one or more portions of image data of the query medical image that is analogous to image data of one or more supplementary medical images.

In some embodiments, the processor can be operable to: for each query medical image, generate the identifier that is representative of image data of that query medical image; and for each supplementary medical image, generate the identifier that is representative of image data of that supplementary medical image.

In some embodiments, the processor can be operable to obtain the one or more query medical images from an imaging device.

In another broad aspect, a method of retrieving query medical images from a curated medical image database is disclosed herein. The method can involve operating a processor to: for each of one or more query medical images, determine whether a version of the query medical image is stored in the medical image database, and in response to determining that a version of the query medical image is stored in the medical image database: obtain a curated set of medical images including the query medical image and one or more supplemental medical images; retrieve one or more portions of image data of the query medical image; retrieve a version of a remaining portion of image data of the query medical image; and generate the version of the query medical image using the one or more portions of image data of the query medical image and the version of the remaining portion of image data of the query medical data. The method can also involve operating the processor to, otherwise retrieve the query medical image from the medical image database.

In another broad aspect, a system for retrieving query medical images from a curated medical image database is disclosed herein. The system can include a communication component and a processor in communication with the communication component. The communication component can provide access to the one or more images via a network. The processor can be operable to: for each of one or more query medical images, determine whether a version of the query medical image is stored in the medical image database; and in response to determining that a version of the query medical image is stored in the medical image database, obtain a curated set of medical images including the query medical image and one or more supplemental medical images; retrieve one or more portions of image data of the query medical image; retrieve a version of a remaining portion of image data of the query medical image; and generate the version of the query medical image using the one or more portions of image data of the query medical image and the version of the remaining portion of image data of the query medical data. The processor can also be operable to otherwise retrieve the query medical image from the medical image database.

An example non-transitory computer-readable medium including instructions executable on a processor can implement any one of the methods disclosed herein.

BRIEF DESCRIPTION OF THE DRAWINGS

Several embodiments will now be described in detail with reference to the drawings, in which:

FIG. 3D is an illustration of example initial sets of medical images with similarity indicators;

FIG. 3E is an illustration of example intermediate sets of medical images;

FIG. 3F is an illustration of example intermediate sets of medical images with relevancy indicators;

FIG. 3G is an illustration of example curated sets of medical images;

FIG. 5 is a schematic for searching within a database to locate images with similar image data as a query image, in accordance with an example embodiment;

FIG. 7B is an illustration of an example query image and example plurality of images;

FIG. 7C is an illustration of an example analogous portions of image data of the images of FIG. 7B;

FIG. 7D is an illustration of an example version of the image of FIG. 7B;

FIG. 8B is an illustration of an example query image and an example reference image;

FIG. 8C is an illustration of example image identifiers for the query image and reference image of FIG. 8B;

FIG. 8D is an illustration of an example mosaic created based on the image identifiers of FIG. 8C;

FIG. 8E is an illustration of the example query image and reference image of FIG. 8B with analogous portions identified;

Figure 1:
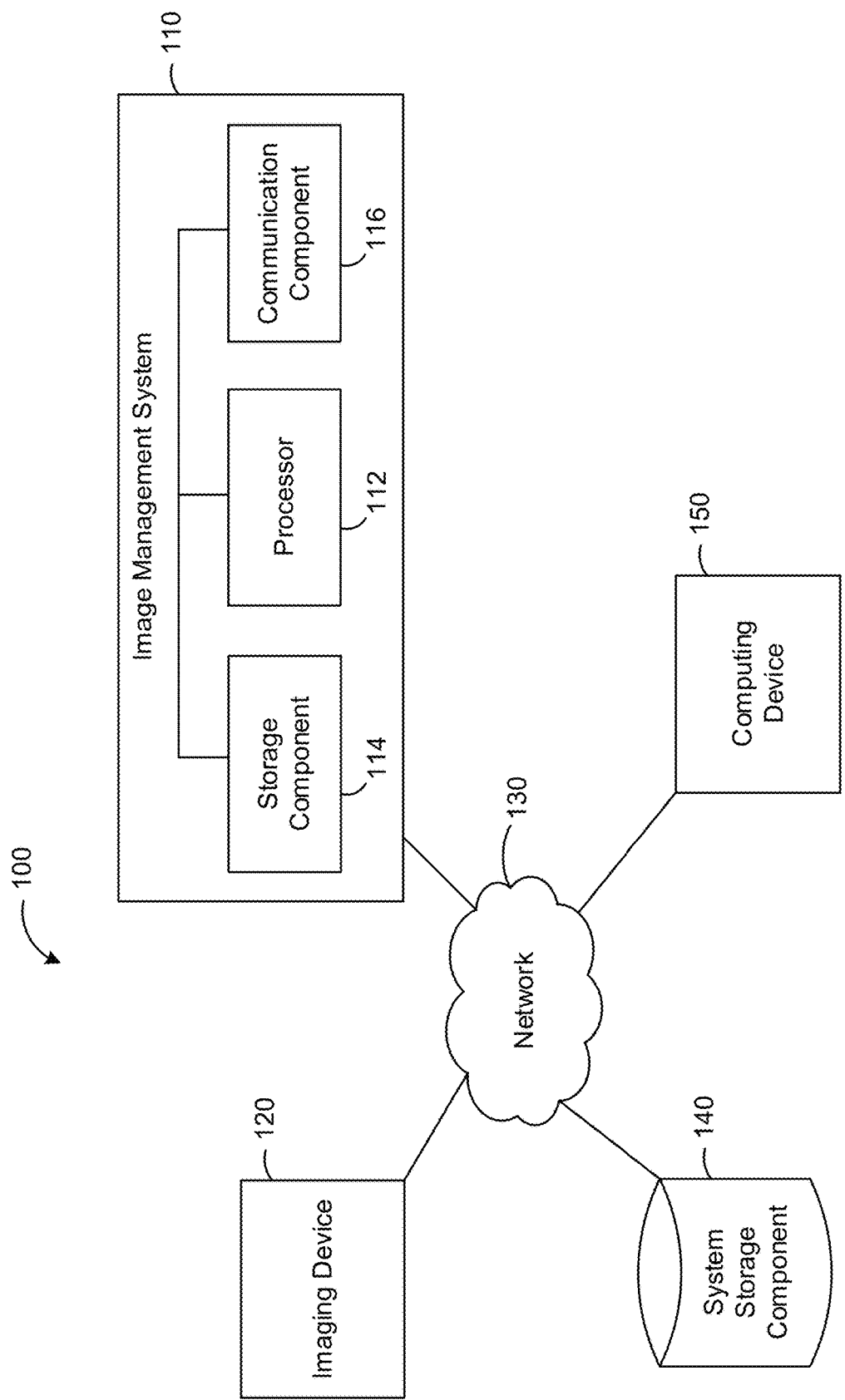
FIG. 1 is a block diagram of an image management system, in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

The various embodiments described herein generally relate to methods (and associated systems configured to implement the methods) for curating images for image databases.

In the medical field, medical images of patients are regularly generated for diagnostic and/or monitoring purposes. Medical images can be generated by many various different imaging devices and undergo visual or numerical investigation for medical diagnoses and research. Modern pathology uses digital scanners to digitize microscopic images of biopsy samples on glass slides in high resolution. These images are called "whole slide images" (WSIs) and are generally large in size (i.e., can be in the order of 100 megabytes and gigabytes).

Medical images are typically archived and may be retrieved for a later purpose (e.g., research or educational). Timely and consistent retrieval of archived images can likely assist with diagnosis. Similarly, many other sectors, such as, but not limited to, architectural and engineering design, geoinformatics, museum and gallery collections, retail catalogs, material processing, military and defense applications, surveillance and forensics, can also benefit from efficient and consistent management of image data.

The ability to efficiently store images, and retrieve those images can be advantageous for these example sectors, amongst others. For example, in the medical field, as medical images are analyzed for a medical diagnosis, the medical images can be compared with archived images of diagnosed cases to assist with the diagnosis. Also, the present diagnosis can benefit from archived images, which may have been clinically evaluated and annotated for second opinions, research, or educational purposes.

Storing digital content can be expensive in view of the large amount of image and video data that can accumulate over time and for high resolution content. For example, the average-sized laboratory processes several thousand patients per year, and the biopsy of every patient can generate multiple glass slides. The storage of digital images has become a major obstacle in the adoption of digital pathology. On average, the cost of network storage can represent approximately 50% to 60% of the cost to deploy a digital pathology workflow.

Notwithstanding the cost of retaining a large volume of images, retrieving images from a large volume of images can be slow. Furthermore, retrieving too many images may result in information overload and may not be useful.

To address the high cost of network storage, some may simply pay the high costs to retain all of their digital images. However, such practice would not distinguish useful digital image data from less useful digital image data. Furthermore, such practice involves paying too much to keep digital images that are not needed.

Alternatively, some may only retain the most recent digital images. That is, to enable storage of new digital content, some practices can involve deleting digital content from old medical cases to make room for new medical cases. For example, older data and data of deceased patients may be discarded to make room for image data of new patients. Likewise, such indiscriminate practices would not distinguish useful digital data (e.g., clinically, research-wise, or educationally relevant) from less useful digital data. For example, discarding data of deceased patients may be valuable for tracking the efficacy of a particular diagnosis and treatment. Thus, such practices may discard valuable information that should be retained.

In some other practices, certain digital content management systems can move old cases to offline storage instead of deleting those cases. However, operating the digital content management systems to retrieve images from offline storage can be too slow and impractical.

Other practices for maintaining a medical image database can involve compressing image data files to reduce the size of the data files. However, image compression can result in a loss of data. Image compression has limited use in medical diagnoses since the reduced image data would unlikely offer the necessary information to assist with the diagnosis.

Reference is first made to FIG. 1, which illustrates an example block diagram 100 of an image management system 110 in communication with an imaging device 120, a system storage component 140, and a computing device 150 via a network 130. Although only one imaging device 120 and one computing device 150 are shown in FIG. 1, the image management system 110 can be in communication with fewer or more imaging devices 120 and fewer or more computing devices 150. The image management system 110 can communicate with the devices 120, 150 over a wide geographic area via the network 130.

The imaging device 120 can include any device capable of capturing image data and/or generating images, and/or storing image data. For example, the imaging device 120 can be a digital pathology scanner.

As shown in FIG. 1, the image management system 110 includes a processor 112, a storage component 114, and a communication component 116. The image management system 110 may include one or more servers that may be distributed over a wide geographic area and connected via the network 130. In some embodiments, each of the processor 112, the storage component 114 and the communication component 116 may be combined into a fewer number of components or may be separated into further components.

The processor 112 may be any suitable processors, controllers, digital signal processors, graphics processing units, application specific integrated circuits (ASICs), and/or field programmable gate arrays (FPGAs) that can provide sufficient processing power depending on the configuration, purposes and requirements of the image management system 110. In some embodiments, the processor 112 can include more than one processor with each processor being configured to perform different dedicated tasks.

The processor 112 may be configured to control the operation of the image management system 110. The processor 112 can include modules that initiate and manage the operations of the image management system 110. The processor 112 may also determine, based on received data, stored data and/or user preferences, how the image management system 110 may generally operate.

The processor 112 can pre-process images. For example, the processor 112 can operate to stitch frames received from the imaging device 120 together to produce a whole slide image (i.e., digitized glass slide). The processor 112 can also, or alternatively, apply different processing techniques to the frames, including, but not limited to, field flattening, de-Bayering, sharpening, de-noising, color correction, and compression. The image management system 110 can then store the whole slide image into the storage component 114, for example. The image management system 110 can receive the frames directly from the imaging device 120—that is, the pre-processing component can be optional.

The processor 112 can generate image identifiers for each image. An image identifier can represent a content of the image that it is associated with. That is, an image identifier represents at least a portion of the image data of that image. For example, the image data (e.g., select features and/or portions) can be translated by the image management system 110 into an encoded representation as the image identifier. For example, the image identifier can be a numerical representation containing integer values and/or binary values.

By translating and storing the image data in association with image identifier, the processor 112 can then search the associated image data by searching a database of the associated image identifiers. For example, the processor 112 can compare and retrieve similar or related images by searching a database of the associated image identifiers. The database of the associated image identifiers can include a set of image identifiers for images for the purpose of comparison with other indexed images. Typically, the database of image identifiers relates to images of the same modality. For example, a database of image identifiers can relate to human anatomical histopathology whole slide images with hematoxylin and eosin (H&E) staining. Each set of image identifiers defined for an image can be a function of the type and content of the image. A set of image identifiers can include one or more image identifiers. In some embodiments, a set of image identifiers can include hundreds of image identifiers for an image.

When indexing an image, the processor 112 can populate the storage component 114 or the system storage component 140 with the image and/or the image identifier. For example, the communication component 116 can receive the image from the imaging device 120. The processor 112 can then process the image to generate an image identifier and store the image identifier along with the image. In some embodiments, the image identifier may be embedded as metadata in the image file. In some embodiments, the image identifiers can be stored separately from the images.

The processor 112 can operate to search the storage component 114 and/or the system storage component 140 using an image query based on the image identifier generated. As the image identifier represents a portion of each of the image, the image identifier includes less data than the complete frame or whole image. Searching with the image identifier can be faster than searching with the data associated with the complete frame or whole image.

The processor 112 can curate images for the database. For example, the processor 112 can determine whether to store the images in the database. The processor 112 can determine whether to store an image in the database when the image is received from the imaging device 120. The processor 112 can also determine whether an image in the database should continue to be stored in the database. For example, the processor 112 can process an existing database and determine whether each image should be retained. In some embodiments, the processor 112 can determine that an existing image that is currently stored in the database can be deleted upon processing another image—for example, that new image may contain more relevant or useful image data than the existing image.

In addition to determining whether to store images, the processor 112 can determine how to store images. For example, the processor 112 can determine that an image should be stored in a manner that reduces the amount of storage space required. For example, the processor 112 can process the image to generate a version of that image that requires less data for storage.

For example, images with high resolution are typically associated with large data files while images with lower resolution are associated with smaller data files size. The processor 112 can determine that an image or portions of the image originally having a high resolution can be stored at a lower resolution. Images stored with a lower resolution, in part or whole, are referred to herein as versions of the image. In some embodiments, high resolution can relate to a magnification of 20× or 40× while low resolution can relate to a magnification of less than 20×. For example, storing a version of a whole slide image having regions of interest saved at an original high magnification of 20× or 40× and remaining portions of the image at a low magnification of less than 10× can result in a reduction of the image file size from gigabytes to megabytes.

In order to determine whether and how to store an image, the processor 112 can analyze the similarity and relevancy of the image with respect to related images in the database.

When searching for an image and retrieving the image, the processor 112 can generate an image query based on the image identifier and initiate a search for the associated image in the storage component 114 or the system storage component 140. The image query generated by the processor 112 can search the storage component 114 or the system storage component 140 for similar image identifiers. The retrieved similar image identifiers can direct the processor 112 to the related images and/or reports associated with the related images stored in the storage component 114 or in the system storage component 140. The processor 112 can retrieve the related image and/or associated report with an image query search, for example.

In some embodiments, the processor 112 can determine a degree of similarity between image identifiers by comparing the bit values between the image identifiers. For example, the processor 112 can determine a degree of similarity between the image identifiers by applying a Hamming distance calculation. Other methods for calculating a degree of similarity are possible.

The image(s) associated with the stored image identifiers identified by the processor 112 as similar can be useful to the user requesting the image query search by the image management system 110. In the medical imaging context, a medical professional (radiologist, pathologist, diagnostician, researcher, etc.) may scan a patient and use the image to search for more information about the patient's illness.

For example, the processor 112 can receive an image query that defines a size, shape, and location of a tumor. In some embodiments, the image query can originate from the computing device 150. The processor 112 can then initiate a search for images that satisfy that image query. When the image management system 110 receives the search results, the communication component 116 can display the resulting images to the user for review. In some embodiments, the resulting images can be displayed at the computing device 150. The image management system 110 can provide further information in respect of the results for the user, such as the medical case information of each result. Accordingly, the user can see how previous patients with a similar tumor were diagnosed, treated and evaluated.

The processor 112 can generate a report based on the imaging data received from the imaging device 120. For example, the reporting component can identify similar reports from the storage component 114 and extract relevant report data from the identified reports for generating the report for the imaging data received from the imaging device 120. An example report can include data related to various characteristics including, but not limited to, procedure type, specimen focality, tumor site, tumor focality, microscopic features of tumor, histologic type, histologic features, and histologic grade.

In some embodiments, the processor 112 can be separated into further components such as a pre-processing component, an indexing component, a searching component, and a curating component, which can be combined into a fewer number of components or may be separated into further components. Each component may also be implemented with hardware or software, or a combination of both. For example, one or more components can include computer programs executable by the processor 112 to conduct the relevant operations.

The communication component 116 may be any interface that enables the image management system 110 to communicate with other devices and systems. In some embodiments, the communication component 116 can include at least one of a serial port, a parallel port or a USB port. The communication component 116 may also include at least one of an Internet, Local Area Network (LAN), Ethernet, Firewire, modem, fiber, or digital subscriber line connection. Various combinations of these elements may be incorporated within the communication component 116.

For example, the communication component 116 may receive input from various input devices, such as a mouse, a keyboard, a touch screen, a thumbwheel, a track-pad, a track-ball, a card-reader, voice recognition software and the like depending on the requirements and implementation of the image management system 110.

The storage component 114 can include RAM, ROM, one or more hard drives, one or more flash drives or some other suitable data storage elements such as disk drives, etc. The storage component 114 is used to store an operating system and programs, for example. For instance, the operating system provides various basic operational processes for the processor. The programs include various user programs so that a user can interact with the processor to perform various functions such as, but not limited to, viewing and/or manipulating the image data as well as retrieving and/or transmitting image data as the case may be.

In some embodiments, the storage component 114 can store the images, information related to image identifiers of the images, information related to curation of the database, and information related to the imaging devices 120.

The storage component 114 may include one or more databases (not shown) for storing image data, information relating to the image data, such as, for example, patient data with respect to the image data, information related to reports associated with the images, such as, for example, diagnoses with respect to the image data. For example, the storage component 114 can store image identifiers for the images. Each image identifier can also be associated with additional information, such as but not limited to information on the tissue type and cancer type, and can be accompanied by relevant pathology reports. When a search conducted by the image management system 110 identifies an image identifier with associated reports, a later review of the initial query image by the pathologist can benefit from the associated reports.

The storage component 114 can also store curation information about the images. Curation information can include information about related images, information about the similarity of related images in the database and the relevancy of related images in the database.

Similar to the storage component 114, the system storage component 140 can store images and information related to images. Images and information related to images can be stored in the system storage component 140 for retrieval by the computing device 150 or the image management system 110.

Images described herein can include any digital image with any number of pixels. The images can have any size and resolution. In some embodiments, the size and resolution of the image can be adjusted in one or more pre-processing stages. Example image pre-processing includes normalizing the pixel dimensions of an image and digital filtering for noise reduction.

An example image is a medical image of a body part, or part of a body part.

A medical image can be generated using any modality, including but not limited to microscopy, X-ray radiography, magnetic resonance imaging (MRI), ultrasound, and/or computed tomography scans (CT scans). Microscopy can include, but is not limited to whole slide imaging, reflected light, brightfield, transmitted light, fluorescence, and photoluminescence.

The image can be a black and white, grey-level, RGB color, or false color image. An image data structure typically includes an intensity value at each pixel location. To capture a wide dynamic range of intensity values, the data structure of the image uses a number of data bits to represent each pixel.

Sub-images, or patches, can also be defined within images. The dimensions of a sub-image are generally smaller than the dimensions of the image itself. For example, sub-image can be defined as a small image for the purpose of dividing a larger image into a smaller size. For example, for a larger image that is larger than 5000×5000 pixels, a sub-image can be defined as being 1000 pixels by 1000 pixels. In some embodiments, a sub-image can overlap with a neighboring sub-image—that is, a sub-image can include the same pixels as another sub-image of the same image. In some embodiments, sub-images of the same image may not overlap. For example, for an image of a 10 mm×10 mm tissue area (captured at 0.5 µm pixel resolution or 20× magnification), 400 non-overlapping sub-images having a size of 1000×1000 pixels can be defined.

In some embodiments, processing a plurality of sub-images can be faster than processing the image itself. In some embodiments, sub-images can contain unique features of the larger image that can be distinguished from other sub-images of the same larger image.

An image can belong to a dataset, that is, collection of related images that are composed of separate elements that can be accessed and processed individually or in combination by a processor 112 for the purpose of organizing them into groups or sets of similar images. For example, pathology brightfield whole slide images with hematoxylin and eosin staining can form a dataset of related images from different organs of the human body, Other example datasets can include fluorescence images of mouse brain tissue sections, or fluorescence images of immunohistochemical images for cancer diagnosis.

Information related to image identifiers of images that may be stored in the storage component 114 or the system storage component 140 may, for example, include but is not limited to the patches, features detected in the patches, clusters, representative sub-images of the clusters, features detected in the representative patches, encoded representations of the representative patches, including encoded representations containing integer values and/or binary values, such as barcodes. Barcodes can be, for example, a one-dimensional or a two-dimensional binary representation of unique image features for the purpose of creating an index to represent an image. Binary representations of image features can be generated by a thresholding algorithm of image feature vectors to map real-valued numbers to zeros and ones. Barcodes are generally used for computational purposes and a visual representation, such as a traditional barcode having a plurality of parallel lines of varying widths, can also be generated if necessary. Generally, an image can be represented by a finite number of barcodes.

Information related to image annotations that may be stored in the storage component 114 or the system storage component 140 may, for example, include but is not limited to text comments, audio recordings, markers, shapes, lines, free form mark-ups, and measurements.

Information related to imaging devices that may be stored in the storage component 114 or the system storage component 140 may, for example, include but is not limited to a device identifier, a device location, a device operator, a modality, supported image resolutions, supported image file types, image size range, image margin ranges, and an image scale range.

Information related to image subjects that may be stored in the storage component 114 or the system storage component 140 may, for example, include but is not limited to a patient identifier, a date of birth, gender, home address, primary physician, and medical team in the case of medical images.

Information related to the curated image database that may be stored in the storage component 114 or the system storage component 140 may, for example, include but is not limited to a similarity indicator and a relevancy indicator.

In some embodiments, the image management system 110 can receive images directly from the imaging device 120. For example, the image management system 110 can read images directly from a storage component of the imaging device 120. The image management system 110 may process query images, generate image identifiers, and retrieve similar images in real-time or nearly in real-time, as the query images are being received from the imaging device 120. By increasing the speed in which the query image can be reviewed and analyzed with respect to an archive of images in real-time, or near real-time, the image management system 110 can improve patient care and responsiveness.

In the context of the present disclosure, the terms "real-time" or "near real-time" is defined as image processing that is concurrent to, or within a small temporal window of, the query image acquisition or generation. The purpose of real-time or near real-time image processing is to deliver search and retrieval results from the image management system 110 to the user within seconds or minutes after a medical imaging scan of the patient. Accordingly, related medical case information may be delivered to the patient's doctor with minimal delay, for a timely diagnosis of the patient's illness.

In some embodiments, images can be loaded into the image management system 110 from the system storage component 140 or computing device 150 that is remote from the image management system 110. For example, the image management system 110 may be used to process offsite data. Processing offsite data or non-time-sensitive data can assist with various applications, such as research applications where real-time processing is not necessary, and/or medical diagnostic applications at areas (e.g., remote areas, underprivileged areas, underdeveloped areas, etc.) where real-time processing is not possible, or nearly impossible due to unreliable or slow communication networks. For research applications, a researcher tasked with processing hundreds or thousands of medical images would still benefit from the increased processing speed of the image management system 110 over conventional feature-based detection CBIR systems, even if the hundreds or thousands of medical images are not related to any patients awaiting diagnosis. In areas with unreliable and/or slow communication networks (e.g., remote areas, underprivileged areas, underdeveloped areas, etc.), the methods and systems described herein can facilitate retrieval of the related images even with the unreliable and/or slow communication networks.

The computing device 150 may be any networked device operable to connect to the network 130. A networked device is a device capable of communicating with other devices through a network such as the network 130. A network device may couple to the network 130 through a wired or wireless connection.

The computing device 150 may include at least a processor and memory, and may be an electronic tablet device, a personal computer, workstation, server, portable computer, mobile device, personal digital assistant, laptop, smart phone, WAP phone, an interactive television, video display terminals, gaming consoles, and portable electronic devices or any combination of these.

In some embodiments, the computing device 150 may be a laptop, or a smartphone device equipped with a network adapter for connecting to the Internet. In some embodiments, the connection request initiated from the computing device 150 may be initiated from a web browser and directed at the browser-based communications application on the image management system 110.

The network 130 may be any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these, capable of interfacing with, and enabling communication between, the image management system 110, the imaging device 120, the system storage component 140, and the computing device 150.

Figure 2:
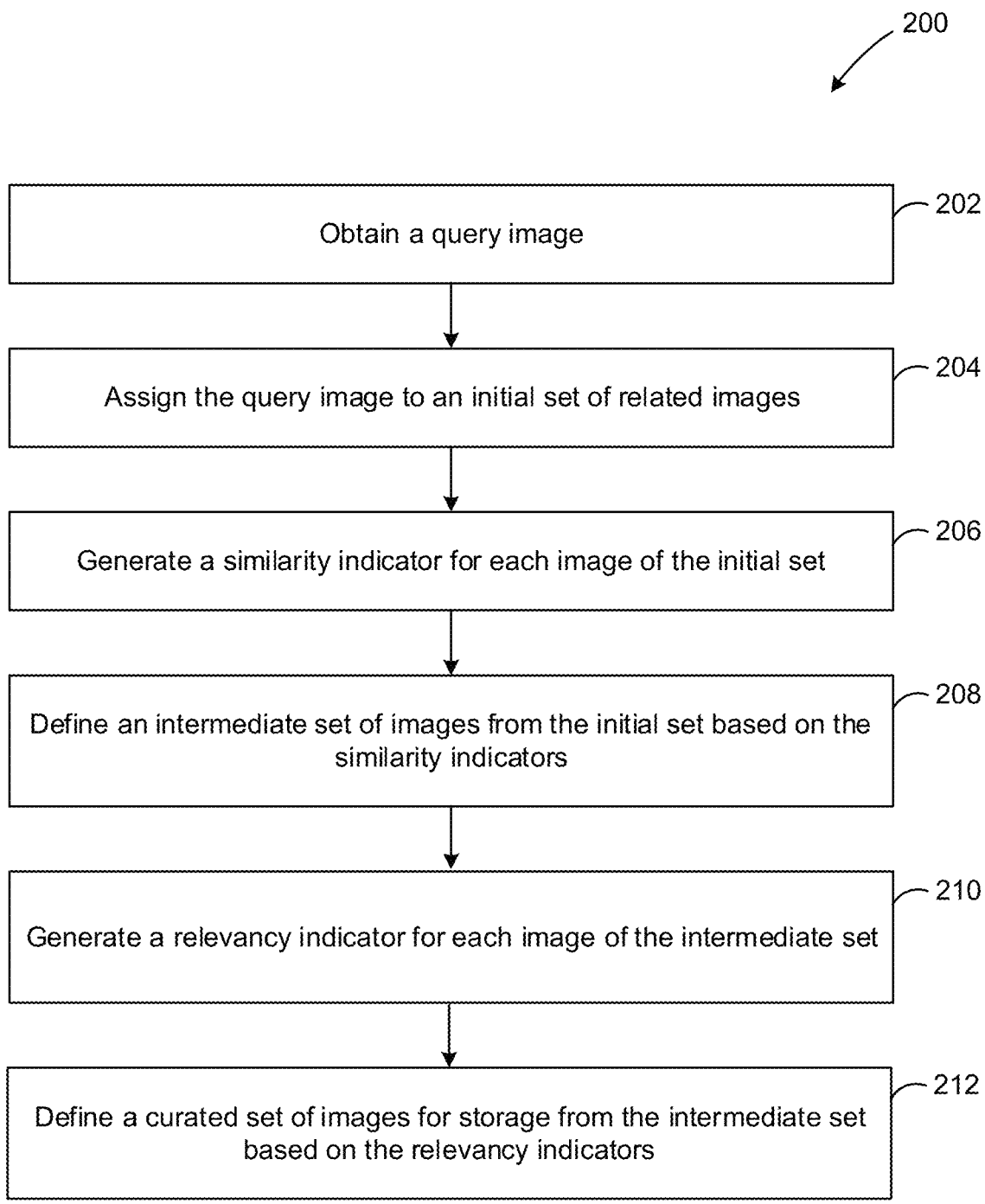
FIG. 2 is a flowchart of a method of curating images for an image database, in accordance with an example embodiment.

Referring now to FIG. 2, an example method 200 of curating images for an image database is shown in a flowchart diagram. To assist with the description of the method 200, reference will be made simultaneously to FIG. 3A to FIG. 3G. An image management system, such as image management system 110 having a processor 112 can be configured to implement method 200.

Figure 3C:
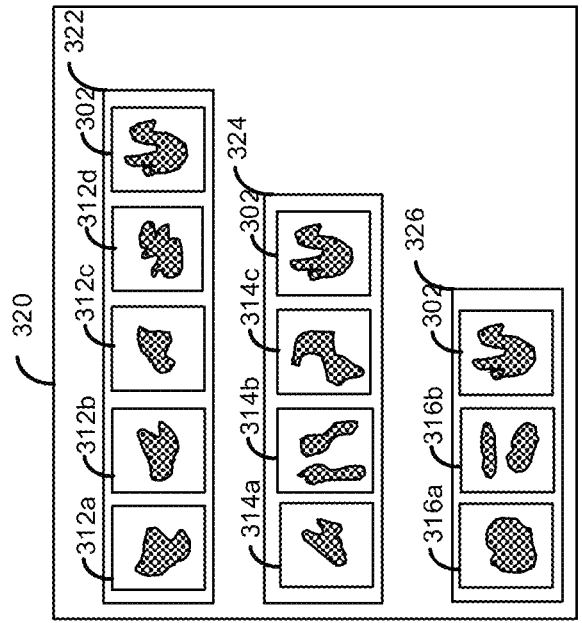
FIG. 3C is an illustration of example initial sets of medical images.
Figure 3B:
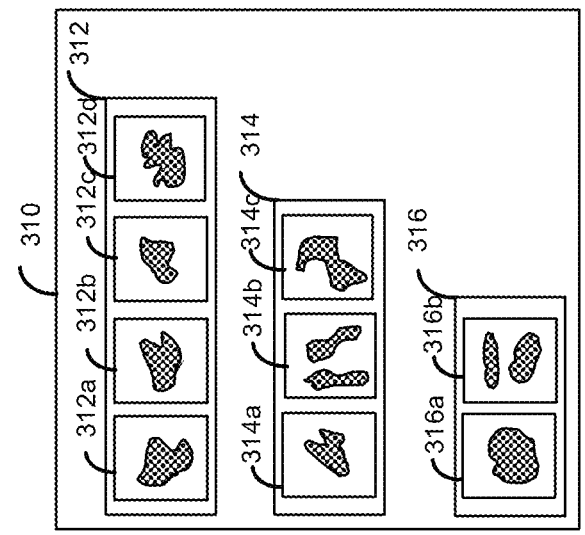
FIG. 3B is an illustration of example related medical images.
Figure 3A:
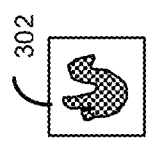
FIG. 3A is an illustration of an example query medical image.

Method 200 can begin at 202, when the processor 112 obtains a query image, such as example image 302 in FIG. 3A. Although image 302 is shown in FIG. 3A as being a medical image, and in particular, a histopathology image, the image 302 can be any image. Furthermore, although only one query image 302 is shown in FIG. 3A, the processor 112 can obtain one or more query images. The one or more query images can be obtained from an imaging device 120, a computing device 150, or a system storage component 140. The term "query image" used herein refers to an image for the purpose of using as an input to an index operation or a search operation performed by a processor, such as processor 112.

The processor 112 can generate an image identifier for each of the query images 302. As described above, the image identifier is a representation of the image data of the query image 302. The processor 112 can store the image identifiers for the query image in the system storage component 140.

In some embodiments, the image identifier may be stored in the system storage component 140, and the processor 112 can obtain the image identifier stored in the system storage component 140. For example, if the query image is obtained from the system storage component 140, the image identifier may be stored in the system storage component 140 as well.

The processor 112 can use the image identifier of the query image 302 to search the image database for related images 310 having similar image data as that of the query image 302. In some embodiments, the processor 112 can search the image database for related images 310. The processor 112 can retrieve related images based on a degree of similarity between the image identifier of the query image and the image identifier of a supplemental image. In some embodiments, the processor 112 can determine a degree of similarity that represents a distance between image identifiers. That is, the degree of similarity can represent a quantification of a difference between two given sets of bit values that represent indices for the purpose of similarity measurement of images.

Furthermore, the processor 112 can locate images with similar image data within the related images 310 to create one or more sets of related images for each query image 302.

FIG. 3B shows an example of three sets of related images for query image 302, namely three sets of related images 312, 314, and 316. While only nine related images are shown in FIG. 3B for illustrative purposes, fewer or more related images can be located by the search. Furthermore, while only three sets of related images are shown in FIG. 3B for illustrative purposes, the related images located by the search can be grouped into fewer or more sets of related images. The number of sets of related images for a query image 302 can depend on the size of the dataset to which the query image 302 belongs, the size of the database being searched, the diversity of images within the dataset to which the query image 302 belongs, and/or the diversity of images within the database being searched.

Each set of related images can include any number of images. In FIG. 3B, for illustrative purposes, a first set of related images 312 includes four images 312a, 312b, 312c, and 312d; a second set of related images 314 includes three images 314a, 314b, and 314c; and a third set of related images 316 includes two image 316a and 316b.

Images may be grouped in sets in the image database based on shared characteristics or a combination of shared characteristics. For example, images can be grouped based on an image type and/or a diagnosis of a particular condition.

Since the sets of related images are located based on the identifier for the query image 302, the processor 112 assigns the query image 302 to each set of related images at 204. In the example of FIG. 3C, the query image 302 is assigned to each of the three sets of related images (312, 314, and 316 of FIG. 3B) to provide initial sets 320 of related images 322, 324, and 326 of FIG. 3C.

As shown in FIG. 3C, the first initial set of related images 322, includes the query image 302 and supplemental images 312a, 312b, 312c, and 312d from the first set 312 of FIG. 3B. Similarly, the second initial set of related images 324, includes the query image 302 and supplemental images 314a, 314b, and 314c from the second set 314 of FIG. 3B and the third initial set of related images 326, includes the query image 302 and supplemental images 316a and 316b from the third set 316 of FIG. 3B.

At 206, for each of the initial sets 320 of related images 322, 324, and 326, the processor 112 generates a similarity indicator for each image of the initial sets to provide sets 330 shown in FIG. 3D. The similarity indicator can be representative of a degree of similarity or dissimilarity between image data of a single image within the initial set of images and all image data of that initial set of images. The degree of similarity between image data can be determined by comparing bit values of the image data of an image within the set of images and the image data of the set of images. In some embodiments, the degree of similarity between image data may be determined with a Hamming distance calculation.

In some embodiments, the similarity indicator can be a normalized distance within each initial set of images. In some embodiments, the similarity indicator can be normalized similarity indicators determined by the processor 112 when searching for related images. The processor 112 can determine a smallest degree of similarity and a largest degree of similarity within an initial set. The processor 112 can use the difference between the smallest and largest degrees of similarity to normalize the degrees of similarity for each image of the initial set. As a result, the similarity indicators can have a value within a range of 0% to 100%. For example, the smallest degree of similarity and the largest degree of similarity within each of initial sets 322, 324, and 326 can be used to calculate normalized distance values (i.e., the similarity indicators) between 0% and 100% for each initial set of images.

FIG. 3D shows an example of the initial sets with similarity indicators 332, 334, and 336. As shown in FIG. 3D, set 332 includes images 312a, 312b, 312c, 312d, and 302 with similarity indicators 94%, 82%, 96%, 91%, and 98%, respectively. Likewise, the processor 112 can generate similarity indicators 92%, 84%, 95%, and 97% for images 314a, 314b, 314c, and 302 for the second initial set 334, respectively. As well, the processor 112 can generate similarity indicators 92%, 96%, and 78% for images 316a, 316b, and 302 of the third initial set 336. FIG. 3D also shows how the processor 112 generates a similarity indicator for the query image 302 in each of the three initial sets 332, 334, and 336, and thus, the query image 302 has three different similarity indicators.

At 208, for each initial set of related images 332, 334, and 336, the processor 112 defines an intermediate set of images from the initial set based on the similarity indicator of each image of the initial set. The intermediate set of related images 340 in FIG. 3E are a subset of the initial set of related images 320 in FIG. 3C with greater similarity.

To define an intermediate set of images 340 from the initial set with similarity indicators 330, the processor 112 can compare the similarity indicators to a similarity threshold. The processor 112 can determine whether the similarity indicator for that image exceeds a similarity threshold. If the similarity indicator for that image exceeds the similarity threshold, the processor 112 can assign that image to the intermediate set. For example, and not of limitation, if the similarity indicators can have a value within a range of 0% to 100%, the similarity threshold can have a value of 80%. The similarity threshold can be varied depending on various factors, such as but not limited to, the type of image, the intended medical diagnosis, and/or the size of the database.

FIG. 3E shows examples of intermediate sets 340 defined from the initial sets 332, 334, and 336 of FIG. 3D, respectively. In this example, a similarity threshold of 90% is used for illustrative purposes; however the similarity threshold can be a greater or lesser value.

The similarity indicator for image 312b of the first initial set 332 of FIG. 3D does not exceed the similarity threshold. Meanwhile, the similarity indicators for images 312a, 312c, 312d, and 302 of the first initial set 332 of FIG. 3D are greater than the similarity threshold. Therefore, the processor 112 defines a first intermediate set 342 as including images 312a, 312c, 312d, and 302. Image 312b of the first initial set 332 is excluded from the first intermediate set 342.

Likewise, the similarity indicator for image 314b of the second initial set 334 of FIG. 3D does not exceed the similarity threshold and the similarity indicators for images 314a, 314c, and 302 of the second initial set 334 of FIG. 3D are greater than the similarity threshold. As a result, a second intermediate set 344 includes images 314a, 314c, and 302 of the second initial set 334 of FIG. 3D. Image 314b of the second initial set 334 is excluded from the second intermediate set 344.

As well, the similarity indicator for image 302 of the third initial set 336 of FIG. 3D does not exceed the similarity threshold. Meanwhile, the similarity indicators for images 316a and 316b of the third initial set 336 of FIG. 3D are greater than the similarity threshold. As a result, a third intermediate set 346 includes images 316a and 316b of the third initial set 336 of FIG. 3D. Image 302 of the third initial set 336 is excluded from the third intermediate set 346.

At 210, for each of the intermediate sets 340 of images 342, 344, and 346, the processor 112 generates a relevancy indicator for each image of the intermediate set to provide intermediate sets 350 of images having relevancy indicators, as shown in FIG. 3F. The relevancy indicator can be representative of a degree of the relevancy between the image and the intermediate set to which the image belongs. The degree of relevancy is representative of correlations between a plurality of relevant parameters, or domain knowledge parameters, associated with the image and the intermediate set.

The relevancy indicator can be a normalized relevance value within each intermediate set of images. In some embodiments, the relevance value can be generated by the processor 112 based on a set of relevance parameters for the images. The relevance parameters can be, for example, domain knowledge parameters. The processor 112 can determine a smallest relevance value and a largest relevance value within an intermediate set. The processor 112 can use the difference between the smallest and largest relevance values to normalize the relevance values for each image of the intermediate set. As a result, the relevancy indicators can have a value within a range of 0% to 100%. For example, the smallest relevance values and the largest relevance values within each of intermediate sets 342, 344, and 346 can be used to calculate normalized relevance values (i.e., the relevancy indicators) between 0% and 100% for each set.

FIG. 3F shows an example of intermediate sets with relevancy indicators 352, 354, and 356. As shown in FIG. 3F, set 352 includes images 312a, 312c, 312d, and 302 with relevancy indicators 62%, 18%, 96%, and 81%, respectively. Likewise, the processor 112 can generate similarity indicators 93%, 94%, and 85% for images 314a, 314c, and 302 for the relevancy intermediate set 354, respectively. As well, the processor 112 can generate similarity indicators 72% and 96% for images 316a and 316b of the third intermediate set 356.

FIG. 3F shows how the query image 302 can be assigned to two intermediate sets 352 and 354. Furthermore, the processor 112 can generate a relevancy indicator for the query image 302 in each of the two intermediate sets 352 and 354, and thus, the query image 302 can have two different relevancy indicators.

At 212, for each intermediate set of images 342, 344, and 346, the processor 112 defines a curated set of images for storage in the image database from the images in the intermediate set based on the relevancy indicator of each image. The curated set of images 360 are a subset of the intermediate set of images 350 with greater relevancy.

In some embodiments, the processor 112 can define the curated set of images 360 for storage based on a first relevancy threshold for the relevancy indicator. For example, the processor 112 can determine whether the relevancy indicator for an image exceeds a first relevancy threshold. If the relevancy indicator of the image does not exceed the first relevancy threshold, the processor 112 can exclude the image from the curated set of images 360. Otherwise, the processor 112 can assign the image to the curated set of images 360. For example, and not of limitation, if the relevancy indicators can have a value within a range of 0% to 100%, the first relevancy threshold can have a value of 20%. The first relevancy threshold can be varied, depending on various factors, such as but not limited to, the type of image, the intended medical diagnosis, and/or the size of the database.

FIG. 3G shows an example of curated sets 360 defined from the intermediate sets 352, 354, and 356 of FIG. 3F, respectively. In this example, a first relevancy threshold of 20% is used for illustrative purposes; however the first relevancy threshold can be a greater or lesser value.

The relevancy indicator for image 312c of the first intermediate set 352 of FIG. 3F does not exceed the first relevancy threshold. Meanwhile, the relevancy indicators for images 312a, 312d, and 302 of the first intermediate set 352 of FIG. 3F are greater than or equal to the first relevancy threshold. Therefore, the processor 112 defines a first curated set 362 as including images 312a, 312d, and 302. Likewise, the relevancy indicators for images 314a, 314c, and 302 of the second intermediate set 354 of FIG. 3F are greater than or equal to the first relevancy threshold and as such, a second curated set 364 is defined as including images 314a, 314c, and 302. Furthermore, the relevancy indicators for images 316a and 316b of the third intermediate set 356 of FIG. 3F are greater than or equal to the first relevancy threshold and as such, a third curated set 366 is defined as including images 316a and 316b.

In the example of FIG. 3G, the query image 302 is included in the first and second curated sets 362 and 364. That is, the processor 112 can determine that the query image 302 should be stored in the image database. In some embodiments, the query image 302 can be excluded from the curated sets of images 360. That is, the processor 112 can determine that the query image 302 should not be stored in the image database. For example, the processor 112 can determine that the similarity indicator does not exceed the similarity threshold or that the relevancy indicator does not exceed the first relevancy threshold (such as, for example, 312c of FIG. 3E). In some embodiments, the processor 112 can also store the similarity indicator and/or the relevancy indicator for the query image 302 in the image database, such as a similarity indicator database and a relevancy indicator database, respectively.

In some embodiments, the processor 112 can temporarily store the query image 302. Upon determining that the query image 302 should be excluded from the curated sets of images, the processor 112 can delete the query image 302.

One or more supplemental images can be excluded from the curated set of images 360. For example, the processor 112 can determine that by assigning the query image 302 to the first curated set 362, supplemental images 312b and 312c can be discarded from 312. Furthermore, if supplemental image 312c is not assigned to any other set of related images, such as curated sets of images 354 and 356, in the image database, supplemental image 312c may be discarded from the image database.

In some embodiments, the processor 112 can also determine how to store an image in the curated set of images 360. For example, the processor 112 can determine that an image can be stored in its original format, or that a version of the image can be stored in a different format. The version of the image having a different format can use less data. It can be desirable to use less data to store images containing less relevant or useful information. Accordingly, it can be desirable to store images containing relevant information in their original format and store versions of images containing less relevant information in a different format. The images can be any one of the query image 302 and/or one or more supplemental images 312a, 312b, 312c, 312d, 312e, 314a, 314b, 314c, 314d, 316a, 316b, and 316c in the curated set of images 360.

In some embodiments, the processor 112 can determine how to store an image based the relevancy indicator of an image. The processor 112 can compare the relevancy indicator to a second relevancy threshold. If the relevancy indicator of the image exceeds the second relevancy threshold, the processor 112 can determine that the image should be stored in its original format in the curated set of images 360. Otherwise, the processor 112 can determine that a version of that image having a different format should be stored in the curated set of images.

FIG. 3G shows an example of curated sets of images 360 containing images stored in different formats. In this example, a second relevancy threshold of 80% is used for illustrative purposes however the second relevancy threshold can be a greater or lesser value. Since the relevancy indicator of images 312*d*, 314*a*, 314*c*, 316*b*, and 302 exceeds the second relevancy threshold, images 312*d*, 314*a*, 314*c*, 316*b*, and 302 in their original format can be included in the curated set of images 360. While the relevancy indicator of images 312*a* and 316*a* exceed the first relevancy threshold, they do not exceed the second relevancy threshold. As such, images 312*a* and 316*a* can be included in the curated set of images 360 but only as versions 362*a* and 366*a* of the images 312*a* and 316*a* as shown in FIG. 3G, respectively.

In this example, upon processing another image, such as image 302, the processor 112 can determine that existing images 312*a* and 316*a* that are stored in the database should be stored as versions 362*a* and 366*a* of the images.

In some embodiments, the second relevancy threshold is equal to the first relevancy threshold. When the second relevancy threshold is equal to the first relevancy threshold, a version of each image that is not included in the curated set 360 can be included in the curated set 360. In some embodiments, the second relevancy threshold is higher than the first relevancy threshold. When the second relevancy threshold is higher than the first relevancy threshold, neither the images nor versions of the images having a relevancy indicator less than the first relevancy threshold can be included in the curated set 360; versions of the images having a relevancy indicator greater than the first relevancy threshold but less than the second relevancy threshold can be included in the curated set 360; and the images having a relevancy indicator greater than the second relevancy threshold can be included in the curated set 360.

Figure 4:
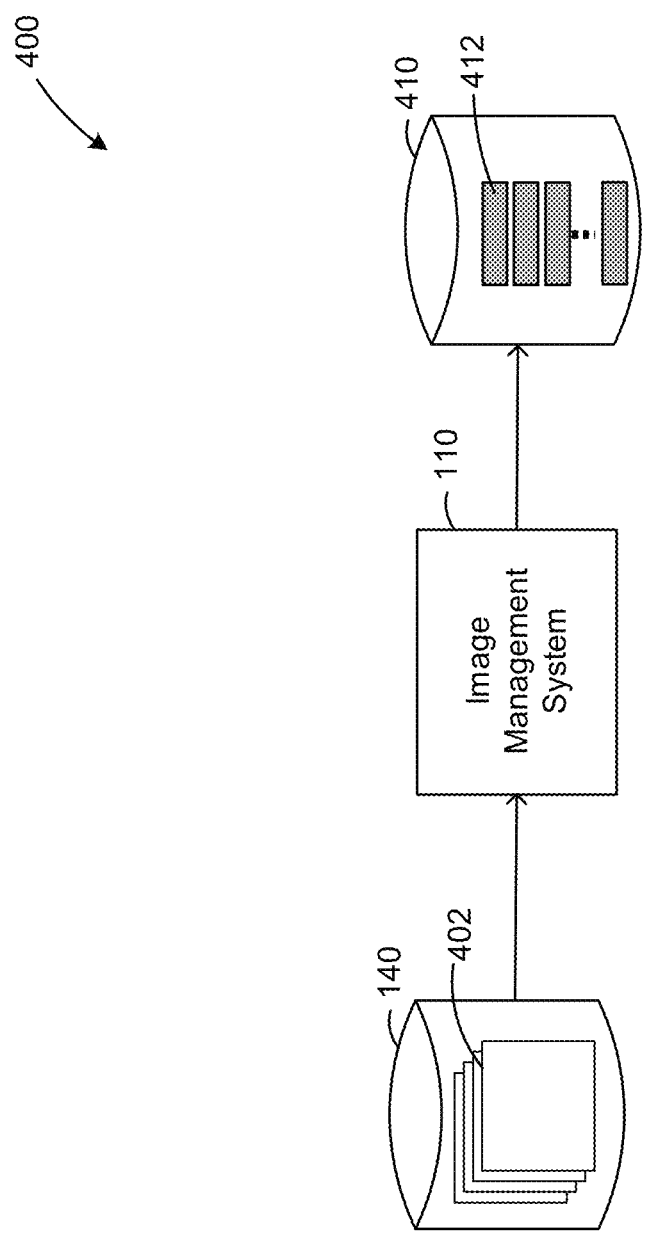
FIG. 4 is a schematic for generating image identifiers for a plurality of images, in accordance with an example embodiment.

Referring now to FIG. 4, shown therein is a schematic 400 illustrating an example of generating image identifiers for a plurality of images. Image identifiers can be used in the method 200 to locate images with similar image data within a database. The schematic 400 shows the generation of image identifiers 412 for a plurality of images 402. In other embodiments, an image identifier can be generated for a single image, such as a newly acquired image.

The plurality of images 402 can be stored in a database as an unindexed archive of images. As shown in FIG. 4, the plurality of images 402 can be stored in a storage component, such as system storage component 140. While the plurality of images 402 are shown as being stored in a single storage component for illustrative purposes, the plurality of images 402 can be stored in a plurality of storage components distributed over a network. The image management system 110 can access the plurality of images 402 in the system storage component 140.

The image management system 110 can use a processor, such as processor 112 (not shown in the schematic 400), to generate a plurality of image identifiers 412 for the plurality of images 402. One or more image identifiers can be generated for each image. Any appropriate techniques can be used for generating the image identifiers, including but not limited to segmentation, clustering, deep networks, and binarization algorithms. The image identifiers 412 can be stored in a storage component, such as storage component 410 dedicated to storing image identifiers. While FIG. 4 shows the storage component 410 as being a different storage component than the storage component in which the images are stored, in some embodiments, the image identifiers can be stored in the same storage component as the images. That is, in some embodiments, the image identifiers 412 can be stored in a storage component that is not dedicated to storing image identifiers, such as system storage component 140. While the plurality of image identifiers 412 are shown as being stored in a single storage component for illustrative purposes, the plurality of image identifiers 412 can be stored in a plurality of storage components distributed over a network.

The processor 112 can generate image identifiers for each image of the plurality of images sequentially, or in parallel. When the processor 112 generates image identifiers for two or more images in parallel, the processor 112 can receive the two or more images simultaneously and generate image identifiers for each of the images simultaneously. When the processor 112 generates image identifiers for two or more images sequentially, the processor 112 can receive a first image and generate one or more image identifiers for the first image. Only after generating the one or more image identifiers for the first image, the processor 112 can receive a second image and generate one or more image identifiers for the second image.

Referring now to FIG. 5, shown therein is a schematic 500 illustrating an example search within a database to locate images with similar image data as a query image. Method 200 can involve locating images with similar image data in order to assign the query image to an initial set of related images at 204. The example schematic 500 shows the location of a plurality of images 530 for a query image 502.

The query image 502 can be a single query image, such as query image 302 of FIG. 3A to FIG. 3G. The database can be an indexed archive of images, such as the plurality of images 520. As shown in FIG. 5, the plurality of images 520 can be stored in a storage component, such as system storage component 140. While the plurality of images 520 are shown as being stored in a single storage component for illustrative purposes, the plurality of images 520 can be stored in a plurality of storage components distributed over a network.

An image identifier for the query image 502 and the plurality of images 520 can be stored in a storage component, such as storage component 510. Storage component 510 can be a storage component dedicated to storing image identifiers, such as storage component 410, or a storage component that also stores the plurality of images 520, such as system storage component 140. In other embodiments, the image identifier for the query image 502 is not stored and instead, the image management system 110 can generate an image identifier for the query image 502.

The image management system 110 can receive the query image 502 and the image identifier 512 for the query image and access the plurality of images 520 in the system storage component 140. The image management system 110 can use a processor, such as processor 112 (not shown in schematic 500), to locate a plurality of images 530 for the query image 502 based on the image identifier 512 and the image identifiers for the plurality of images 520. While FIG. 5 shows the plurality of images 530 being four images for illustrative purposes, fewer or more images can be located by the search. When used in method 200, the plurality of images 530 found can be the related images 310 of FIG. 3B.

In some embodiments, the processor 112 can sort the plurality of images 530. In some embodiments, the processor 112 can sort the plurality of images 520 in order of similarity. For example, the processor 112 can sort the plurality of images 520 in order of decreasing similarity to the query image 502.

In some embodiments, the processor 112 can identify one or more portions of image data of the query image 502 that is analogous to image data of an image of the plurality of images 520 having the greatest similarity to the query image. In some embodiments, the processor 112 can use the image identifiers 512 to identify one or more portions of image data of the query image 502 that is analogous to image data of an image of the plurality of images 520. For example, the processor 112 can determine that portions of image data of the query image 502 are similar to portions of image data of an image of the plurality of images 520 based on a measure of similarity between the image identifier for the query image 502 and the image identifier 512 for the image of the plurality of images 520.

It should be noted that the example search shown in FIG. 5 can be implemented with sub-images. That is, query image 502 can be a sub-image of a query image 502 and the plurality of images 520 can be sub-images of one or more images of the plurality of images 520.

Figure 6A:
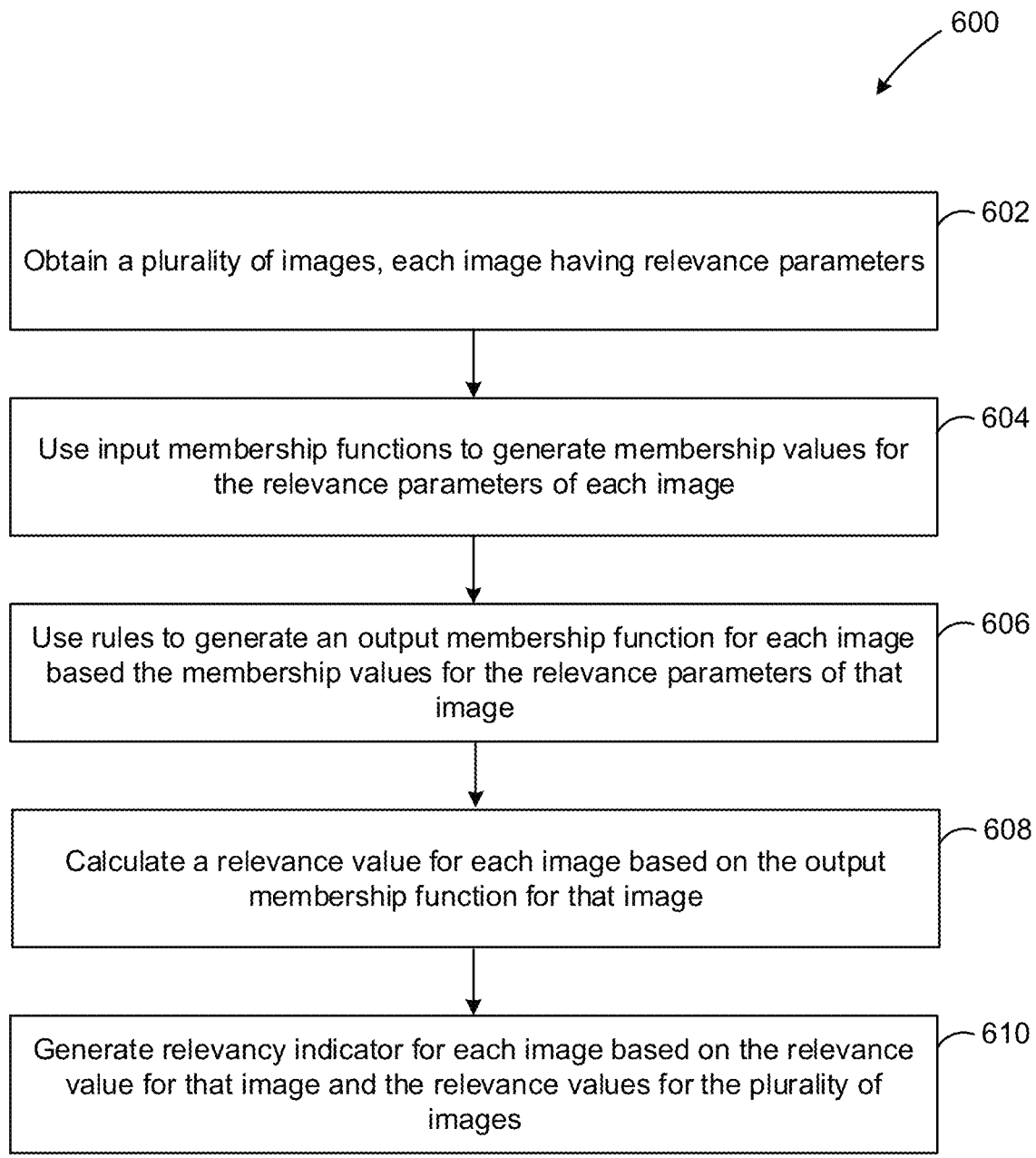
FIG. 6A is a flowchart of a method of generating relevancy indicators for a plurality of images, in accordance with an example embodiment.
Figure 6B:
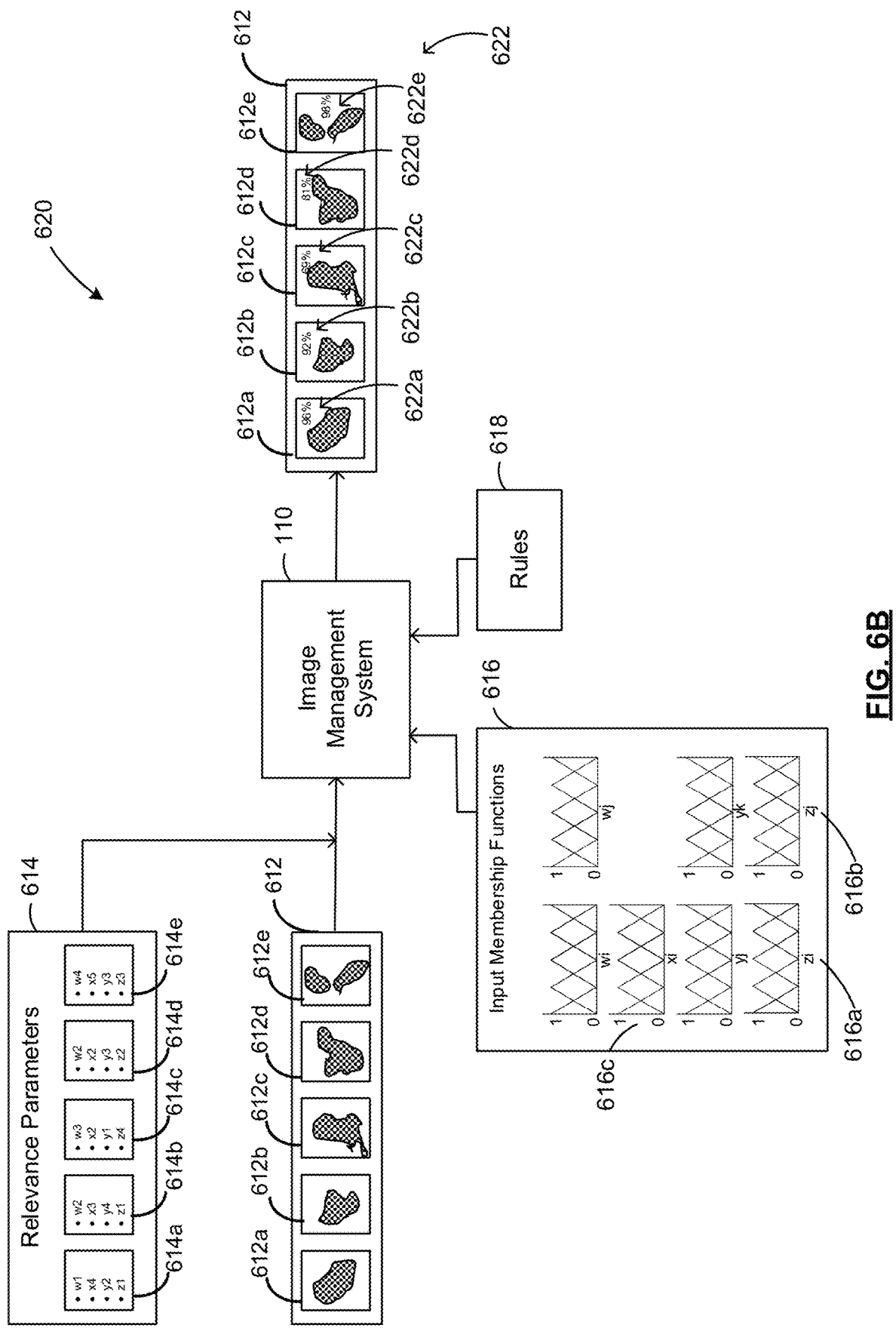
FIG. 6B is an example schematic for the method of FIG. 6A.

Referring now to FIG. 6A, an example method 600 of generating relevancy indicators for a plurality of images is shown in a flowchart diagram. To assist with the description of the method 600, reference will be made simultaneously to FIG. 6B to FIG. 6F. FIG. 6B shows an example schematic 620 illustrating an example generation of relevancy indicators for a plurality of images.

An image management system, such as image management system 110 having a processor 112 (not shown in FIG. 6B) can be configured to implement method 600. As shown in FIG. 6B, the image management system 110 can generate a plurality of relevancy indicators 622 for the plurality of images 612. A relevancy indicator 622a, 622b, 622c, 622d, and 622e is generated for each image 612a, 612b, 612c, 612d, and 612e. In some embodiments, method 600 can be used at 210 of method 200 to generate relevancy indicators for each image of the intermediate set 340.

Method 600 can begin at 602, when the processor 112 (not shown in FIG. 6B) of the image management system 110 obtains a plurality of images and relevance parameters (i.e., domain knowledge parameters) for the plurality of images. For example, as shown in FIG. 6B, the image management system 110 receives a plurality of images 612 and respective domain knowledge parameters 614 for the plurality of images 612. While only five images 612a, 612b, 612c, 612d, and 612e are shown in FIG. 6B for illustrative purposes, the plurality of images can include fewer or more images. Each image 612a, 612b, 612c, 612d, and 612e has a corresponding set of domain knowledge parameters 614a, 614b, 614c, 614d, and 614e, respectively.

Domain knowledge parameters 614 can include quantifiable properties of image datasets and related information. Domain knowledge parameters 614 can depend on the type of image. For example, with histopathology images, domain knowledge parameters 614 can relate to information such as but not limited to a diagnosis date, information about the diagnosing pathologist (e.g., name, seniority, reputation), a degree of rarity of the disease, information about the database (e.g., storage capacity threshold), special case information, information about the acquisition of the image (e.g., stains used) and other information relevant to the image. As shown in FIG. 6B, each image 612a can have domain knowledge parameters 614 such as w, x, y, and z, which can represent, for example, diagnosis date, degree of rarity of the disease, diagnosing pathologist name, and diagnosing pathologist reputation, respectively. As shown in FIG. 6B, the domain knowledge parameters of image 614a are w1, x4, y2, and z1, respectively; the domain knowledge parameters of image 614b are w2, x3, y4, and z1, respectively; the domain knowledge parameters of image 614c are w3 x2, y1, and z4, respectively; the domain knowledge parameters of image 614d are w2, x2, y3, and z2, respectively; and the domain knowledge parameters of image 614e are w4, x5, y3, and z3, respectively.

The plurality of images 612 can be stored in a storage component (not shown in FIG. 6B), such as system storage component 140 or a plurality of storage components distributed over a network 130.

The domain knowledge parameters 614 can be stored in a storage component (not shown in FIG. 6B), such as system storage component 140 or a plurality of storage components distributed over a network 130. The domain knowledge parameters 614 can be stored in a different storage component than that which the plurality of images are stored or the same storage component as the plurality of images. For example, the domain knowledge parameters 614 can be stored as metadata with each image 612a, 612b, 612c, 612d, and 612e.

The image management system 110 can access the plurality of images 612 and the domain knowledge parameters 614 for the plurality of images 612 in the system storage component 140.

Figure 6F:
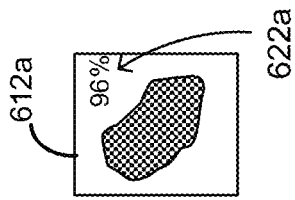
FIG. 6F is an illustration of an example image with a relevancy indicator for the image of FIG. 6C.

At 604, the processor 112 can apply input membership functions, or fuzzy membership functions, to the domain knowledge parameters of each image to generate membership values for the domain knowledge parameters of that image. For example, the processor 112 can receive the domain knowledge parameters 614a for an image 612a, shown in FIG. 6C. The input membership functions, such as input membership functions 616 of FIG. 6B, can be algorithms that assign membership values to each of the domain knowledge parameters. The membership values can be binary (e.g., 0 or 1). Example membership values 632 for an image 612a are shown in FIG. 6D. In some embodiments, the processor 112 can apply multiple input membership functions 616a, 616b for a domain knowledge parameter 614. That is, a domain knowledge parameter 614 can be assigned multiple membership values 632a, 632b shown in FIG. 6D. As shown in the example of FIG. 6B, there can be two input membership functions 616a, 616b, such as zi and zj, for domain knowledge parameter z while there can be one input membership function 616c, such as xi for domain knowledge parameter x.

The input membership functions 616 can be stored in a storage component (not shown in FIG. 6B), such as storage component 114 or system storage component 140. The image management system 110 can access the input membership functions 616 in the storage component 114 or system storage component 140. The input membership functions 616 can be pre-defined. In some embodiments, input membership functions 616 can be defined based on information provided by domain knowledge experts. In some embodiments, input membership functions 616 can be automatically extracted from analysis of historical data using clustering and optimization methods.

Figure 6E:
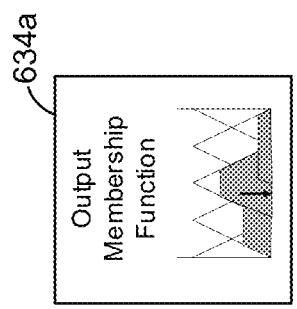
FIG. 6E is an illustration of an example output membership function for the image of FIG. 6C.
Figure 6D:
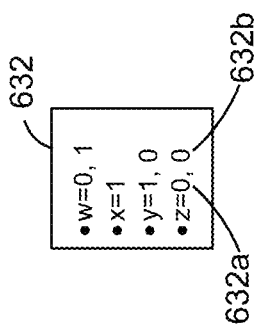
FIG. 6D is an illustration of example membership values for the relevance parameters of FIG. 6C.
Figure 6C:
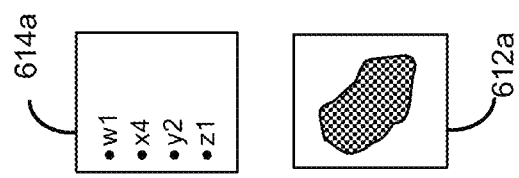
FIG. 6C is an illustration of an example image and example relevance parameters of the image.

At 606, the processor 112 can apply a set of rules, such as rules 618 shown in FIG. 6B, to the membership values 632 of each image 612a to generate an output membership function, such as output membership function 634a of FIG. 6E, for that image 612a.

Rules 618 can be algorithms that assess the entirety of membership values 632 of an image 612a. That is, each rule can analyze membership values 632a, 632b of different domain knowledge parameters 614a to determine an output value. The collection of output values, or fuzzy values, can define an output membership function 634a. Thus, the output membership function 634a is a representation of the degree of membership of the domain knowledge parameters 614.

For example, given domain knowledge parameters w, x, y, and z, a rule can determine an output value based to the membership value of domain knowledge parameter x and z. For example, a first rule can be "If wi is 1 and xi is 0, then the output value y is LOW"; a second rule can be "If wj is 0, yj is 0, and xi is 1, then y is MEDIUM"; and another rules can be "If xi is 1 and zj is 1, then y is HIGH".

In some embodiments, the processor 112 can determine the set of rules 618 prior to step 606. That is, the processor 112 can determine the set of rules 618 prior to applying the rules 618 to the membership values 632. In other embodiments, the set of rules 618 can be pre-defined in tandem with the input membership functions 616. That is, the set of rules 618 correspond to the input membership functions 616.

In some embodiments, the set of rules 618 can be defined based on information provided by domain knowledge experts. In some embodiments, set of rules 618 (can be automatically extracted from analysis of historical data using clustering and optimization methods.

The set of rules 618 can be stored in a storage component (not shown in FIG. 6B), such as storage component 114 or system storage component 140. The image management system 110 can access the set of rules 618 in the storage component 114 or system storage component 140. The set of rules 618 can be stored in a different storage component than that which the input membership functions 616 are stored or the same storage component as the input membership functions 616.

At 608, the processor 112 can calculate a relevance value for each image based on the output membership functions 634a for that image 612a. That is, the output membership function 634a of each image is quantified to obtain a relevance value for each image. The relevance value of an image 612a represents the degree of relevancy of the domain knowledge parameters of an image 612a to the domain knowledge parameters of the plurality of images 612. Furthermore, the relevance value of an image 612a can represent correlations between the domain knowledge parameters 614a associated with the image and the domain knowledge parameters 612 associated with the plurality of images 612. As such, the relevance value of an image 612a can be used to infer the relevancy of the domain knowledge parameters 614a of the image 612a to the domain knowledge parameters 614 of the plurality of images 612.

At 610, the processor 112 can generate a relevancy indicator 622 for each image 612a, 612b, 612c, 612d, and 612e based on the relevance value for that image and the relevance values 622a, 622b, 622c, 622d, and 622e respectively for the plurality of images 612. For example, FIG. 6F shows the relevancy indicator 622a for image 612a. The relevancy indicator 622a can be a normalized relevance value within the plurality of relevance values for the plurality of images 612. The processor 112 can determine a smallest relevance value and a largest relevance value within the plurality of relevance values for the plurality of images 612. The processor 112 can use the difference between the smallest and largest relevance values to normalize the relevance values for each image of the plurality of images. As a result, the relevancy indicators can have a value within a range of 0% to 100%. For example, the smallest relevance value and the largest relevance values for the plurality of images 612a, 612b, 612c, 612d, and 612e can be used to calculate normalized relevance values (i.e., the relevancy indicators) between 0% and 100% for each set. The relevancy indicator can be used to infer the importance of an image 612a within plurality of images 612.

Figure 7A:
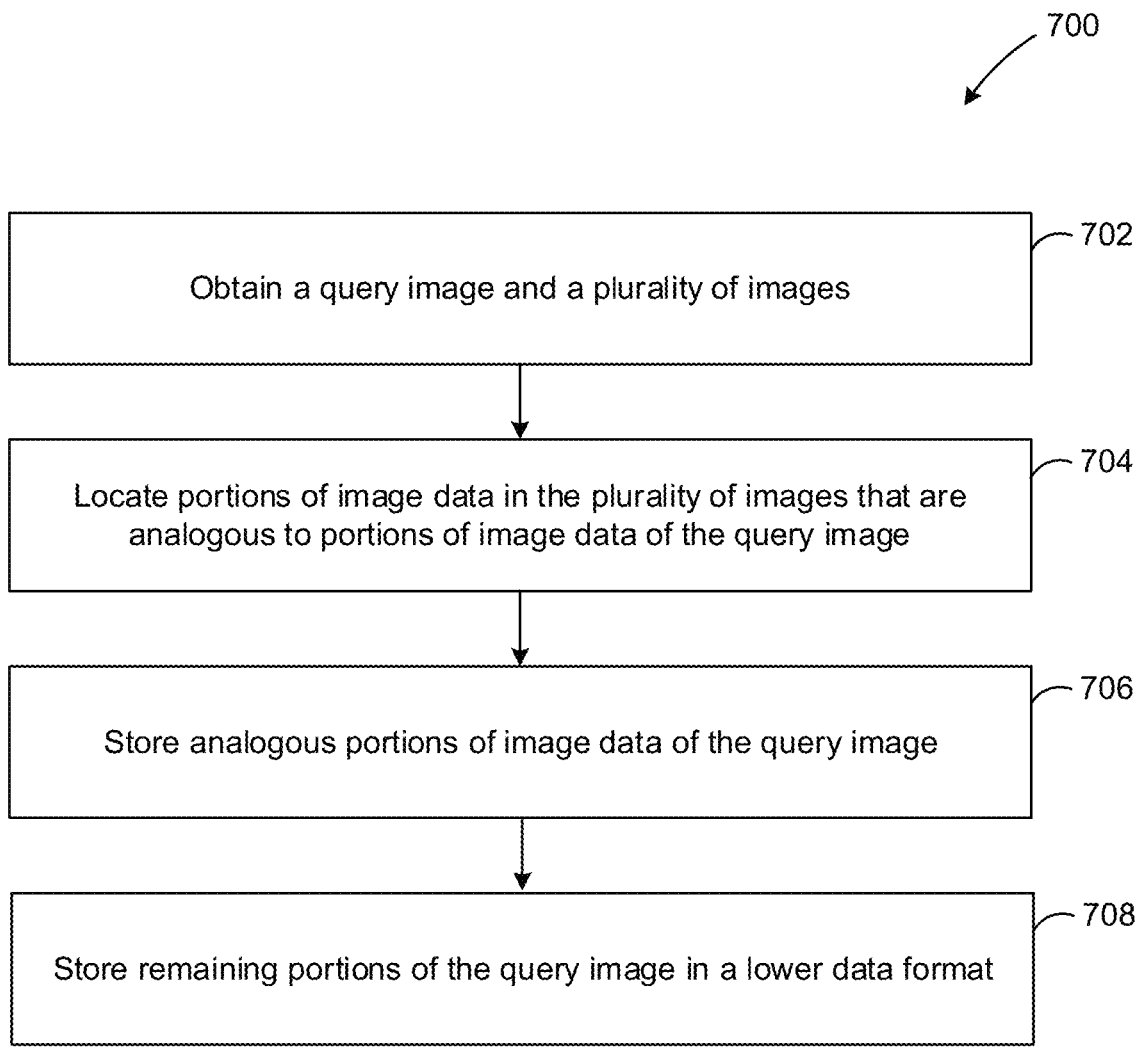
FIG. 7A is a block diagram of a method for generating a version of an image, in accordance with an example embodiment.

Referring now to FIG. 7A, an example method 700 for creating a version of an image is shown in a flowchart diagram. To assist with the description of the method 700, reference will be made simultaneously to FIG. 7B to FIG. 7D.

An image management system, such as image management system 110 having a processor 112, can be configured to implement method 700. Given an image, such as image 710 of FIG. 7B, the image management system 110 can create a version, such as version 720 of FIG. 7D, of the image 710. In some embodiments, method 700 can be used at 212 of method 200 to create a version of an image, such as 362a and 366a, in the curated set of images 360.

Method 700 can begin at 702, when the processor 112 obtains an image 710 and a plurality of reference images 712. The plurality of reference images 712 includes images 712a, 712b, and 712c having similar image data as image 710. In some embodiments, when used within method 200, the image 710 can be an image of the intermediate sets of images 340 and the plurality of reference images 712 can be other images of the intermediate set 342, 344, 346 that the image 710 belongs to. For example, the image 710 can be image 302 and the plurality of reference images 712 can be images 312a, 312c, 312d, 314a, and 314c. In another example, the image 710 can be image 314a and the plurality of reference images 712 can be images 314c and 302.

At 704, the processor 112 can locate portions of image data of the plurality of reference images 712 that is analogous to portions of image data of the query image 710. In some embodiments, the processor 112 can locate one or more patches, or sub-images of the plurality of reference images 712 that is analogous to one or more sub-images of the query image 710. Analogous portions of image data of the plurality of reference images 712 can be located from any image of the plurality of reference images 712. For example, as shown in FIG. 7C, analogous portion 718a of reference image 712b corresponds to portion 716a of the query image 710; analogous portion 718b of reference image 712c corresponds to portion 716b of the query image 710; analogous portions 718c and 718d of reference image 712a correspond to portion 716c and 716d of the query image 710. Furthermore, image data of the plurality of reference images can have similar content. That is, an analogous portion of a first reference image can also correspond to an analogous portion of a second reference image. For example, analogous portion 718b of reference image 712c can have similar content as analogous portion 718c of reference image 712a. As a result, analogous portion 716b can represent similar content as analogous portion 716c.

It should be noted that the analogous portions of image data can have any appropriate size and shape. Furthermore, a query image can have any number of discrete portions of image data with any number of images of the plurality of images. That is, while FIG. 7C shows four portions 716a, 716b, 716c, and 716d of image 710 that are analogous to portions of the plurality of reference images 712 for illustrative purposes, there can be fewer or more portions of image data that is analogous to portions of image data of the plurality of images. As well, while FIG. 7C shows that two portions 716c and 716d in image 710 are analogous to portions 718c and 718d of reference image 712a for illustrative purposes, fewer or more portions of image data of image 710 can be analogous to portions of image data of reference image 712a. Furthermore, while FIG. 7C shows that portions of image data of image 710 are analogous to portions of three reference images 712a, 712b, and 712c of the plurality of reference images for illustrative purposes, fewer or more images of the plurality of reference images 712 can have portions of image data that are analogous to portions of image data of image 710.

The portions 716a, 716b, 716c, and 716d of image data of the query image 710 located at 704 can contain unique features having relevant information. As such, it can be desirable to retain this image data.

At 706, the processor 112 can store the portions 716a, 716b, 716c, and 716d of image data of the query image 710 located at 704 in the database, such as storage component 140. For example, as shown in FIG. 7D, the processor 112 can store patches, or sub-images 722a, 722b, 722c, and 722d of the query image 710, which correspond to portions 716a, 716b, 716c, and 716d of the query image 710 and are analogous to portion 718a of image 712b, portion 718b of image 712c, and portions 718c and 718d of image 712a, respectively. Since this image data can contain relevant information, the sub-images 722a, 722b, 722c, and 722d can be stored in their original format.

The processor 112 can also store an association between analogous portions so that when the query image 710 is displayed, the correspondence to the reference images 712a, 712b, or 712c can be displayed as well and vice versa. That is, one of the reference images 712a, 712b, or 712c are displayed, the correspondence to the query image 710 can be displayed as well.

At 708, the processor 112 can store the remaining portion 724 of the query image 710 in a lower data format in the database. That is, the processor 112 can store the portion 724 of the query image 710 not already stored at 706. This remaining portion 724 may not contain unique features having relevant information. As such, this remaining portion 724 can be stored in a lower data format, such as a lower resolution or reduced magnification.

In some embodiments, the image can be a whole slide image captured at a magnification of 20X or higher. Thus, the portions of image data stored at 706 can be stored at the original magnification of 20X or higher and the remaining portion of image data stored at 708 can be stored at a reduced magnification of less than 20×. The version of the image resulting from the method of 700 includes portions of image data having higher resolution and portions of image data having lower resolution. For example, as shown in FIG. 7D, the stored image 720 includes image data 722a, 722b, 722c, and 722d having a higher resolution and image data 724 having a lower resolution. In some embodiments, storing the version 720 of the image resulting from the method of 700 can require as much as 80% less data than that required to store the original image 710.

Figure 8A:
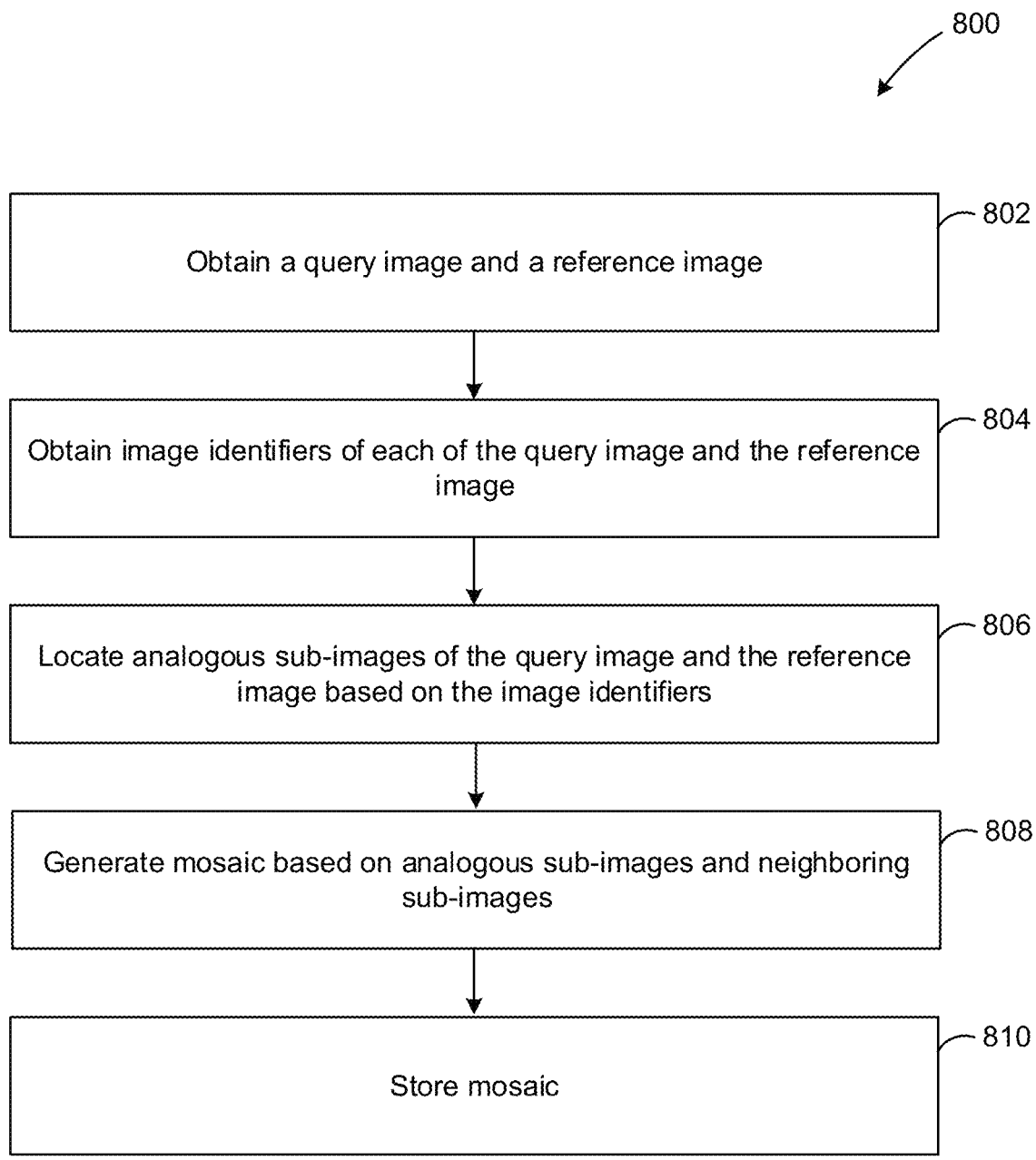
FIG. 8A is a block diagram of a method for locating analogous sub-images, in accordance with an example embodiment.

Referring now to FIG. 8A, an example method 800 for locating analogous portions of image data is shown in a flowchart diagram. To assist with the description of the method 800, reference will be made simultaneously to FIG. 8B to FIG. 8E.

An image management system, such as image management system 110 having a processor 112, can be configured to implement method 800. Given a query image and a reference image, such as images 812 and 822 of FIG. 8B respectively, the image management system 110 can determine whether a portion of the image is analogous to a portion of the image of FIG. 7D, of the image 710. In some embodiments, method 800 can be used at 704 of method 700 to locate portions of image data of each image of the plurality of images that is analogous to portions of image data of the query image. That is, method 800 can be reiterated for each image of the plurality of reference images 712.

Method 800 begins at 802, when the processor 112 obtains the query image 812 and the reference image 822. The query image and reference image can have similar image data. In some embodiments, when used within method 700, query image 812 can be query image 710 and reference image 822 can be an image 712a, 712b, or 712c of the plurality of reference images 712. For example, image 812 can be image 710 and image 822 can be image 712a.

At 804, the processor 112 can obtain image identifiers of each of the query image 812 and the reference image 822. In some embodiments, the image identifier for one or both of the query image 812 and the reference image 822 can be stored and retrieved from a storage component, such as storage component 140. In some embodiments, the processor 112 can generate the image identifier for one or both of the query image 812 and the reference image 822. In some embodiments, the processor 112 can implement the method of the schematic 400 to generate image identifiers.

FIG. 8C illustrates an example image identifier 814 for the query image 812 and an example image identifier 824 for the reference image 822. As shown, each image identifier can include a plurality of sub-images, or patches. For example, image identifier 814 for query image 812 includes 12 patches, 814a, 814b, 814c, 814d, 814e, 814f, 814g, 814h, 814i, 814j, 814k, 814l and image identifier 824 for the reference image 822 includes 12 patches, 824a, 824b, 824c, 824d, 824e, 824f, 824g, 824h, 824i, 824j, 824k, 824l. While 12 sub-images are shown for each of image identifiers 814 and 824 for illustrative purposes, image identifiers can include fewer or more sub-images. Furthermore, while FIG. 8C shows the sub-images of the image identifiers in a 4×3 grid for illustrative purposes, the 4×3 grid is not indicative of the geometric relationship between image data of sub-images. For example, sub-images can overlap (i.e., contain portions of the same information). As well, sub-images that are shown as being adjacent in FIG. 8C may not be adjacent in image 812. Also, the number of sub-images for image 812 and reference image 822 can be different. That is, the number of sub-images for image 812 can be fewer or more than the number of sub-images for reference image 822.

At 806, the processor 112 can locate analogous sub-images of the query image 812 and the reference image 822 based on the image identifiers 814 and 824. In some embodiments, the processor 112 can implement the method of the schematic 500 to locate analogous sub-images between the two images 812 and 822. That is, for each sub-images of image 812, the processor 112 can locate sub-images of image 822 with similar image data as the sub-image. For example, the processor 112 can determine whether any one or more of sub-images 824a to 824l of image 822 are analogous to sub-image 814a of image 812; whether any one or more of sub-images 824a to 824l of image 822 are analogous to sub-image 814b of image 812, and so on. In some embodiments, the processor 112 can find that a sub-image 824a to 824l can be analogous to one or more sub-images 814a to 814l or not analogous to any sub-images 814a to 814l. Furthermore, the processor 112 can find that one or more sub-images 824a to 824l or no sub-images 824a to 824l are analogous to one or more sub-images 814a to 814l.

At 808, the processor 112 can generate a mosaic based on the analogous sub-images located at 806 and neighboring sub-images. To generate a mosaic, the processor 112 can cluster all sub-images of an image into groups, with each sub-image of a group containing similar features for representing the image. The processor 112 can select a plurality of sub-images from the groups. For example, a whole slide image of a 20 mm×20 mm tissue area at 0.5 µm pixel resolution or 20× magnification can contain 1600 non-overlapping patches of 1000×1000 pixels. A mosaic generated for such an image can contain approximately tens to a few hundred sub-images.

The processor 112 can also identify any sub-images that neighbor sub-images of the query image 812 that were found to be analogous with at least one sub-image of the reference image and sub-images that neighbor sub-images of the reference image 822 that were found to be analogous with at least one sub-image of the query image 812.

An example mosaic 830 is shown in FIG. 8D as including sub-images 832 of query image 812 and sub-images 834 of reference image 822. Sub-images 832 include sub-images 814a, 814b, 814c, 814e, 814f, and 814j. Sub-images 834 include sub-images 824a, 824b, 824c, 824e, 824f, 824h, 824i, 824j, and 824l. For example, sub-image 824a of reference image 822 may have been found to be analogous to sub-image 814b of query image 812. Therefore, sub-images 814a, 814c, and 814f which neighbor sub-image 814b are included in the mosaic 830. As well, sub-images 824b, 824e, and 824f which neighbor sub-image 814b are included in the mosaic 830.

At 810, the processor 112 can store the mosaic 830 in a storage component, such as storage component 140. The storage component can be dedicated to storing mosaics or the same storage component in which images 812 and/or 822 are stored. By storing mosaic 830, corresponding portions of the images can be identified for display. For example, as shown in FIG. 8E, portion 836 of image 840 corresponds to sub-images 832 of mosaic 830. Similarly, portion 844 of image 842 corresponds to sub-images 834 of mosaic 830.

Figure 9A:
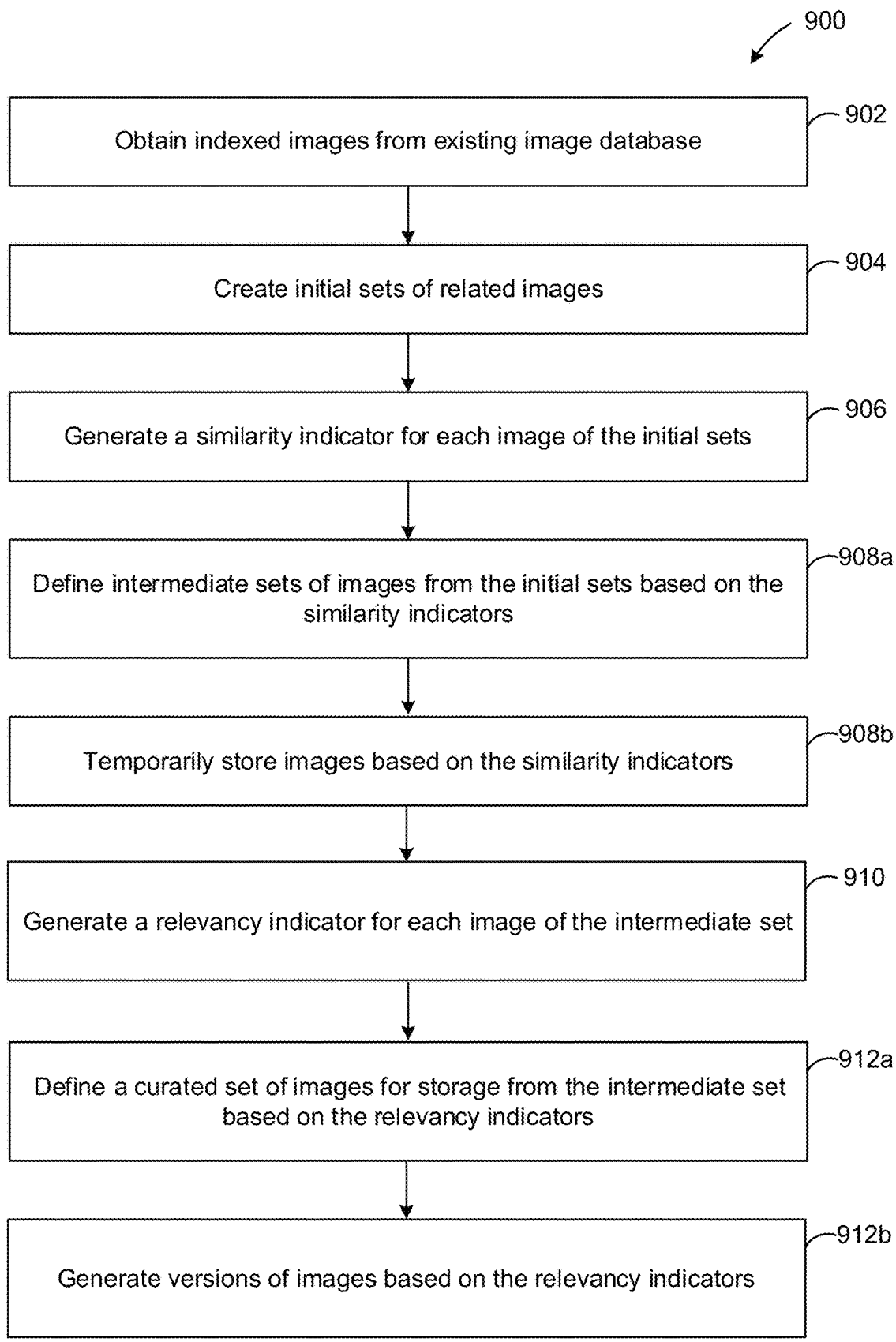
FIG. 9A is a flowchart of an example method of curating images for an image database, in accordance with another example embodiment.
Figure 9B:
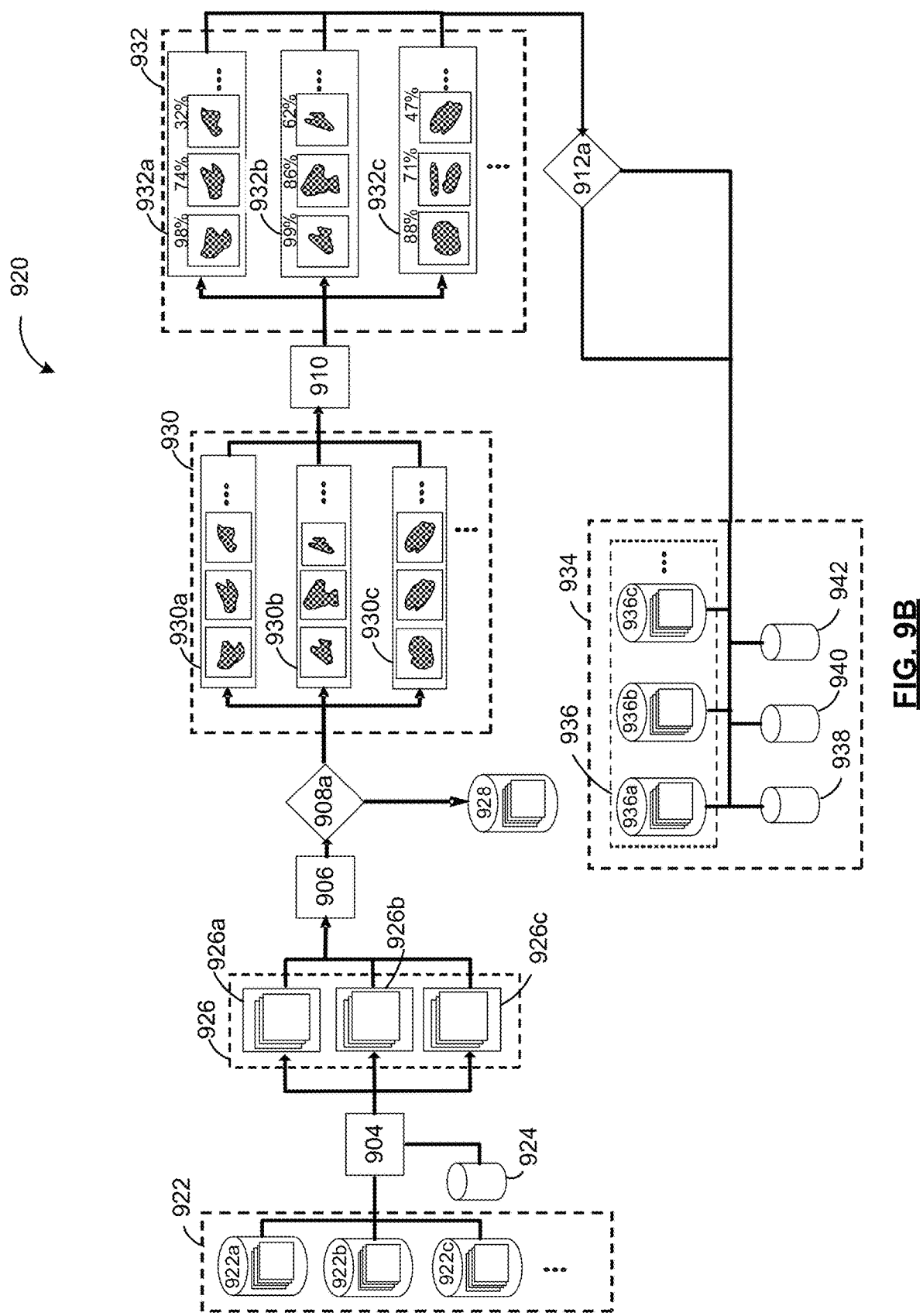
FIG. 9B is an example schematic for the method of FIG. 9A.

Referring now to FIG. 9A, shown therein is an example method 900 of curating an image database is shown in a flowchart diagram. To assist with the description of the method 900, reference will be made simultaneously to FIG. 9B illustrating an example schematic 920 for curating an image database.

An image management system, such as image management system 110 (not shown in FIG. 9B) having a processor 112 (not shown in FIG. 9B) can be configured to implement method 900. The processor 112, the uncurated image database 922, the temporary image database 928, and the curated database 934 are in communication via a network. In FIG. 9B, for illustrative purposes, the image databases 922a, 922b, 922c, 928, the curated image database 936, the uncurated image identifier database 924, the curated image identifier database 938, the similarity indicator database 940, and the relevancy indicator database 942 are shown as separate components but can be combined into a fewer number of components or may be separated into further components, in some embodiments.

Method 900 can begin at 902 when the processor 112 obtains the plurality of images from the existing image database. The existing image database can be the uncurated image database 922 that contains images that are not sorted based on similarity and/or relevancy. While the plurality of images of the uncurated image database are shown as being stored in three storage components 922a, 922b, 922c distributed over a network for illustrative purposes, the plurality of images can be stored in fewer or more storage components.

Images of the uncurated image database may or may not have image identifiers. In some embodiments, at 902, the processor 112 can also generate image identifiers for any images of the uncurated image database that do not have image identifiers. The image identifiers of the plurality of images can be stored in an uncurated image identifier database 924. While the image identifiers of the uncurated image database are shown as being stored in a separate storage component 924 from the plurality of images for illustrative purposes, the image identifiers can be stored in the same storage component 922 as the plurality of images. The processor 112 can use the identifiers for the query images to retrieve related images from the uncurated image database 922.

At 904, the processor 112 can create initial sets of related images using the images retrieved from the uncurated image database 922. Step 904 can be similar to 204 of method 200 in FIG. 2. For example, the initial sets of related images can be initial sets 926 of FIG. 9B. While the plurality of images of the uncurated image database are shown as being assigned to at least three initial sets 926a, 926b, 926c for illustrative purposes, the plurality of images can be assigned to fewer or more initial sets 926.

At 906, the processor 112 can generate a similarity indicator for each image of each initial set of related images. Step 906 can be similar to 206 of method 200 in FIG. 2. The similarity indicator can be normalized for each initial set 926a, 926b, and 926c of the initial sets of related images 926.

At 908a, the processor 112 can define intermediate sets of images from the initial sets based on the similarity indicators generated at 906. Step 908a can be similar to 208 of method 200 in FIG. 2. For example, the intermediate sets of images can be intermediate sets 930 of FIG. 9B. While each of the three intermediate sets 930a, 930b, 930c are shown to include at least three images in FIG. 9B for illustrative purposes, each intermediate set can include fewer or more images.

The processor 112 can determine whether to include each image of an initial set in the corresponding intermediate set based on the similarity indicator and a similarity threshold. If the similarity indicator of an image exceeds the similarity threshold, the image can be retained for the intermediate set. If the similarity indicator of an image does not exceed the similarity threshold, the image can be excluded from the intermediate set.

At 908b, the processor 112 can temporarily store images based on the similarity indicators generated at 906. That is, the processor can store images that are not included in any intermediate set 930 in the temporary image database 928. It should be noted that an image can be included in more than one initial set and therefore can have more than one similarity indicator. If all of the similarity indicators of an image does not exceed the similarity threshold for any of the initial sets that it is in, the processor 112 can store the image in the temporary image database 928.

The processor 112 can automatically delete medical images from the temporary image database 928. In some embodiments, the automatic deletion can be time-based, image quota-based (i.e., number of images), or data capacity-based (i.e., size of image data). In some embodiments, deletion of medical images from the temporary medical image database 928 can require user manual input.

At 910, the processor 112 can generate a relevancy indicator for each image of each intermediate set. Step 910 can be similar to 210 of method 200 in FIG. 2. The relevancy indicator can be normalized for each intermediate set 930*a*, 930*b*, and 930*c* of the intermediate sets of related images 930.

At 912*a*, the processor 112 can define a curated set of images for storage from the intermediate sets 932 having relevancy indicators generated at 910. Step 912*a* can be similar to 212 of method 200 in FIG. 2.

The processor 112 can determine whether to include each image of an intermediate set in the corresponding curated set based on the relevancy indicator and a first relevancy threshold. If the relevancy indicator of an image exceeds the first relevancy threshold, the image can be retained for the curated set. If the relevancy indicator of an image does not exceed the first relevancy threshold, the image can be excluded from the curated set.

At 912*b*, the processor 112 can generate versions of images based on the relevancy indicators generated at 910. If the relevancy indicator of an image exceeds a second relevancy threshold, the image can be retained for the curated set. If the relevancy indicator of an image does not exceed the second relevancy threshold, a version of the image using less data can be stored in the curated set.

The curated sets of images, the image identifiers generated at 902, the similarity indicators generated at 906, and the relevancy indicators generated at 910 can be stored in the curated image database 936 the curated image identifier database 938, the similarity indicator database 940, and the relevancy indicator database 942 of the curated database 934, respectively. In FIG. 9B, for illustrative purposes, the curated database 934 includes a curated image database 936, an image identifier database 938, a similarity indicator database 940, and a relevancy indicator database 942. The curated image database 936, the image identifier database 938, the similarity indicator database 940, and the relevancy indicator database 942 can be combined into a fewer number of databases or may be separated into further databases, in some embodiments. As well, while the plurality of images of the curated image database 936 are shown as being stored in three storage components 936*a*, 936*b*, and 936*c* distributed over a network for illustrative purposes, the plurality of images can be stored in fewer or more storage components.

As shown in method 900, the subject matter disclosed herein can be used to manage an image database by automatically determining: (i) which images contain relevant information; (ii) which images contain information that may be relevant; or (iii) which images contain information that is not relevant. In some embodiments, images containing relevant information can be stored in high-performance storage for fast access; versions of images containing information that may be relevant can be stored in an alternative format using less data and/or in less expensive storage; and images containing information that is not relevant can be deleted. By automatically identifying which images contain relevant information, selectively retaining version of images in alternative formats and excluding images from the database, and deleting images, storage requirements of the database can be reduced without forgoing relevant information. In some embodiments, storage requirements of the database can be reduced by as much as 90% in comparison to retaining all images in the database.

Figure 10A:
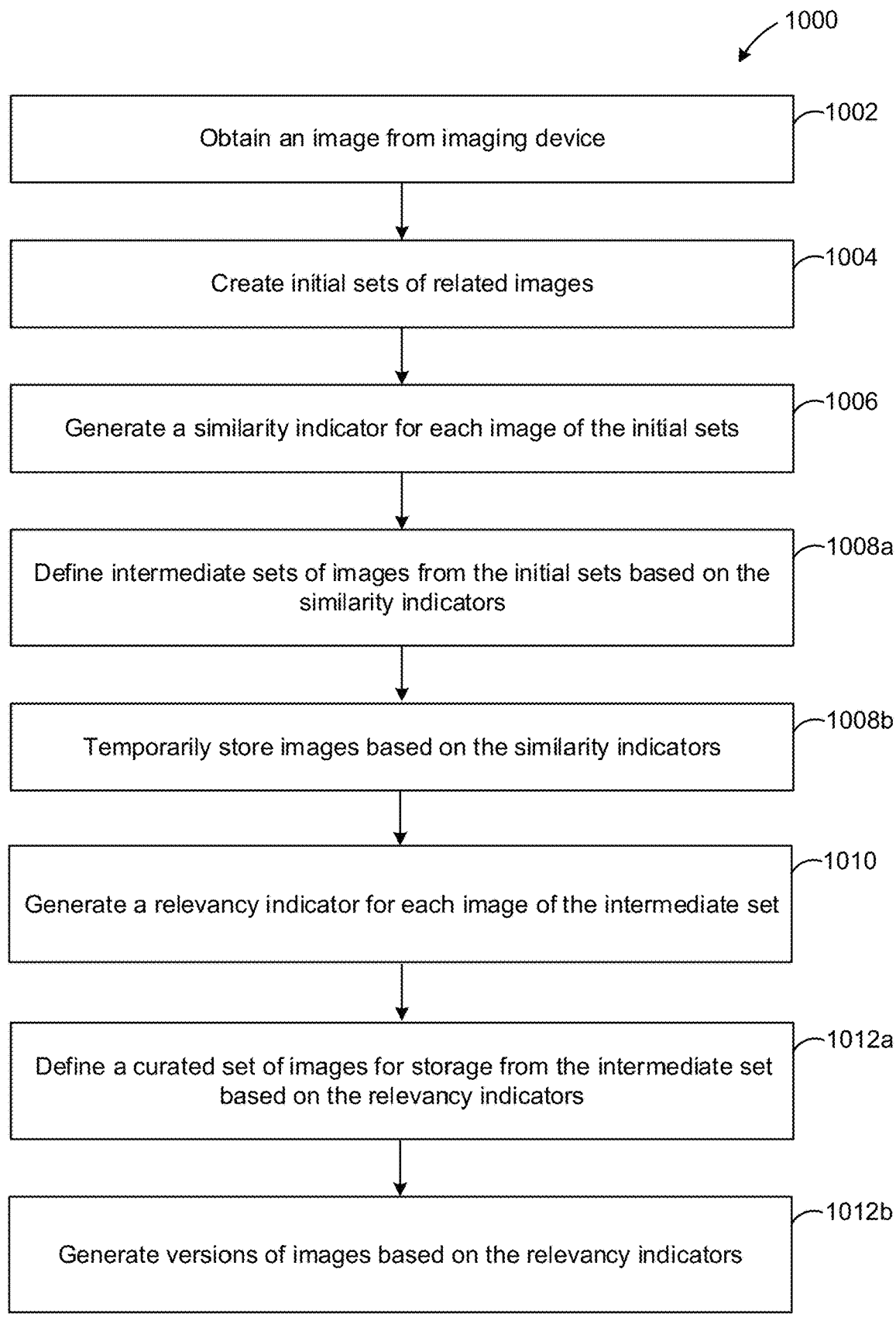
FIG. 10A is a flowchart of an example method of curating images for an image database, in accordance with another example embodiment.
Figure 10B:
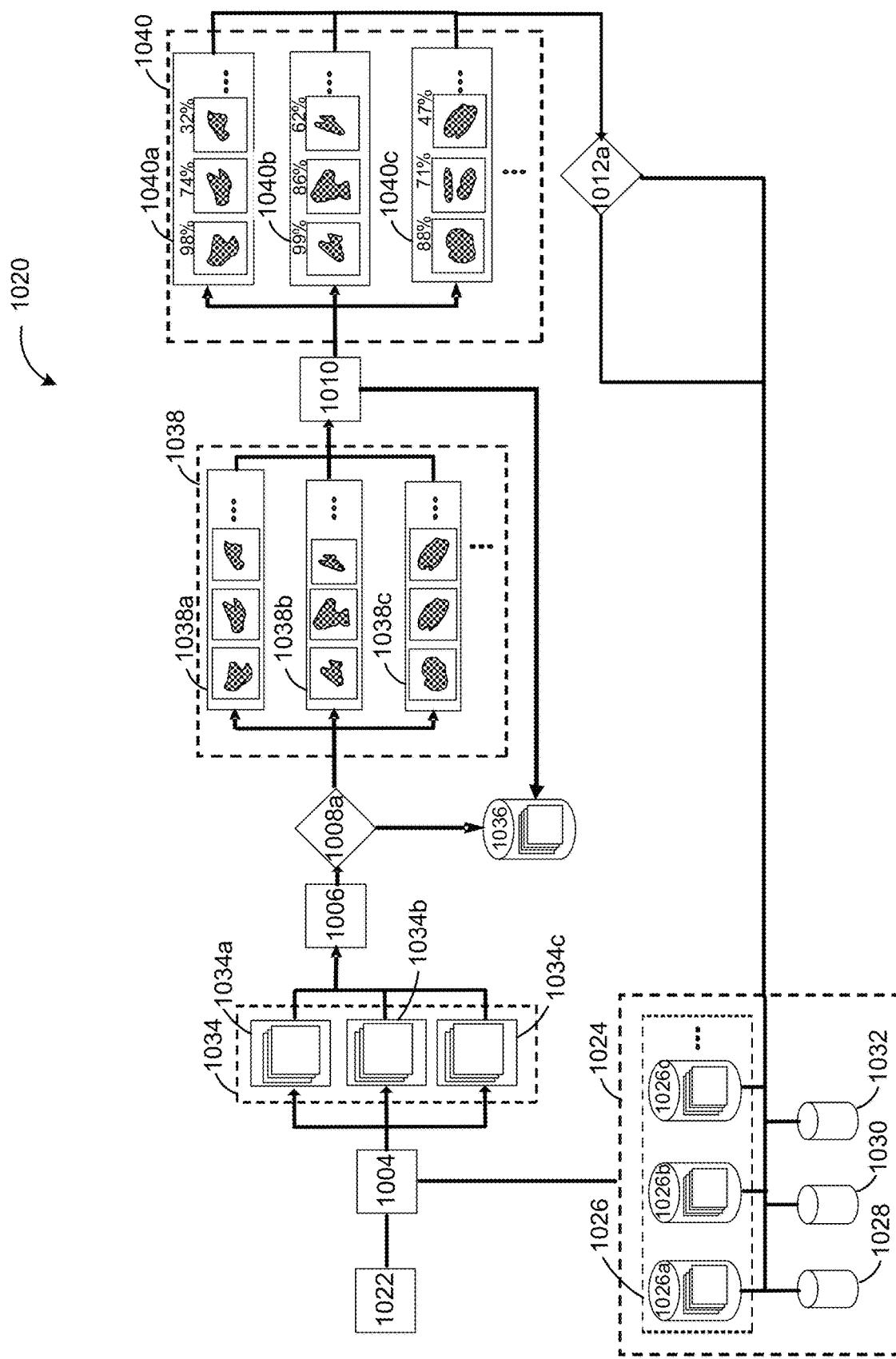
FIG. 10B is an example schematic for the method of FIG. 10A.

Referring now to FIG. 10A, shown therein is an example method 1000 of curating an image for an image database is shown in a flowchart diagram. To assist with the description of the method 1000, reference will be made simultaneously to FIG. 10B illustrating an example schematic 1020 for curating an image for an image database.

An image management system, such as image management system 110 (not shown in FIG. 10B) having a processor 112 (not shown in FIG. 10B) can be configured to implement method 1000. The processor 112, the curated image database 1024 and the temporary image database 1036 are in communication via a network. In FIG. 10B, for illustrative purposes, the image databases 1026*a*, 1026*b*, 1026*c*, and 1036, the curated image identifier database 1028, the similarity indicator database 1030, and the relevancy indicator database 1032 are shown as separate components but can be combined into a fewer number of components or may be separated into further components, in some embodiments.

Method 1000 can begin at 1002 when the processor 112 obtains an image 1022 from an imaging device. The imaging device can be imaging device 120 of FIG. 1.

Since the image 1022 can be newly acquired by the imaging device 120, image 1022 may not have image identifiers. In some embodiments, at 1002, the processor 112 can also generate image identifiers for image 1022. The processor 112 can use the image identifiers for image 1022 to retrieve related images from the curated image database 1024.

At 1004, the processor 112 can create initial sets of related images using the images retrieved from the curated image database 1024. Step 1004 can be similar to 204 of method 200 in FIG. 2. For example, the initial sets of related images can be initial sets 1034 of FIG. 10B. While the plurality of images of the uncurated image database are shown as being assigned to at least three initial sets 1034*a*, 1034*b*, and 1034*c* for illustrative purposes, the plurality of images can be assigned to fewer or more initial sets 1034.

At 1006, the processor 112 can generate a similarity indicator for each image of each initial set of related images. Step 1006 can be similar to 206 of method 200 in FIG. 2. The similarity indicator can be normalized for each initial set 1034*a*, 1034*b*, and 1034*c* of the initial sets of related images 1034.

At 1008*a*, the processor 112 can define intermediate sets of images from the initial sets based on the similarity indicators generated at 1006. Step 1008*a* can be similar to 208 of method 200 in FIG. 2. For example, the intermediate sets of images can be intermediate sets 1038 of FIG. 10B. While each of the three intermediate sets 1038*a*, 1038*b*, and 1038*c* are shown to include at least three images in FIG. 10B for illustrative purposes, each intermediate set can include fewer or more images.

The processor 112 can determine whether to include each image of an initial set in the corresponding intermediate set based on the similarity indicator and a similarity threshold. If the similarity indicator of an image exceeds the similarity threshold, the image can be retained for the intermediate set. If the similarity indicator of an image does not exceed the similarity threshold, the image can be excluded from the intermediate set.

At 1008*b*, the processor 112 can temporarily store images based on the similarity indicators generated at 1006. That is, the processor can store images that are not included in any intermediate set 1038 in the temporary image database 1036. It should be noted that an image can be included in more than one initial set and therefore can have more than one similarity indicator. If all of the similarity indicators of an image does not exceed the similarity threshold for any of the initial sets that it is in, the processor 112 can store the image in the temporary image database 1036.

The processor 112 can automatically delete medical images from the temporary image database 1036. In some embodiments, the automatic deletion can be time-based, image quota-based (i.e., number of images), or data capacity-based (i.e., size of image data). In some embodiments, deletion of medical images from the temporary medical image database 1036 can require user manual input.

At 1010, the processor 112 can generate a relevancy indicator for each image of each intermediate set. Step 1010 can be similar to 210 of method 200 in FIG. 2. The relevancy indicator can be normalized for each intermediate set 1038a, 1038b, and 1038c of the intermediate sets of related images 1038.

At 1012a, the processor 112 can define a curated set of images for storage from the intermediate sets 1040 having relevancy indicators generated at 1010. Step 1012a can be similar to 212 of method 200 in FIG. 2.

The processor 112 can determine whether to include each image of an intermediate set in the corresponding curated set based on the relevancy indicator and a first relevancy threshold. If the relevancy indicator of an image exceeds the first relevancy threshold, the image can be retained for the curated set. If the relevancy indicator of an image does not exceed the first relevancy threshold, the image can be excluded from the curated set.

At 1012b, the processor 112 can generate versions of images based on the relevancy indicators generated at 1010. If the relevancy indicator of an image exceeds a second relevancy threshold, the image can be retained for the curated set. If the relevancy indicator of an image does not exceed the second relevancy threshold, a version of the image using less data can be stored in the curated set.

The curated sets of images, the image identifiers generated at 1002, the similarity indicators generated at 1006, and the relevancy indicators generated at 1010 can be stored in the image databases 1026a, 1026b, and 1026c, the curated image identifier database 1028, the similarity indicator database 1030, and the relevancy indicator database 1032 of the curated image database 1024, respectively. In FIG. 10B, for illustrative purposes, the curated image database 1024 includes a plurality of image databases 1026a, 1026b, and 1026c, an image identifier database 1028, a similarity indicator database 1030, and a relevancy indicator database 1032. The image databases 1026a, 1026b, and 1026c, the image identifier database 1028, the similarity indicator database 1030, and the relevancy indicator database 1032 can be combined into a fewer number of databases or may be separated into further databases, in some embodiments.

As shown in method 1000, upon receipt of a newly-acquired image from an imaging device 120, the subject matter disclosed herein can be used to automatically determine whether the image: (i) contains relevant information; (ii) contains information that may be relevant; or (iii) contains information that is not relevant. In some embodiments, an image containing relevant information can be stored in high-performance storage for fast access; a version of the image containing information that may be relevant can be stored in an alternative format using less data and/or in less expensive storage; and an image containing information that is not relevant can be deleted. By automatically identifying whether the image contains relevant information, selectively retaining a version of the image in an alternative formats and excluding the image from the database, and deleting the image, storage requirements can be reduced without forgoing relevant information.

Since the curated image database 1024 was created prior to the method 1000, the curated image database 1024 is updated to include the curated set of related images. For example, if the query image is assigned to the curated set, the query medical image is stored in the image databases 1026a, 1026b, and 1026c of the curated medical image database 1024. For another example, if a supplementary image stored in the curated image database 1024 prior to the method 1000 is now assigned to the curated set as a version of the medical image, the version of the supplementary image may be stored and the supplementary image itself may be deleted if it is not assigned to any other sets. Furthermore, all similarity indicators and relevancy indicators for the curated set can be stored in the similarity indicator database 1030 and the relevancy indicator database 1032 of the curated image database 1024, respectively.

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers (referred to below as computing devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Various embodiments have been described herein by way of example only. Various modification and variations may be made to these example embodiments without departing from the spirit and scope of the invention, which is limited only by the appended claims. Also, in the various user interfaces illustrated in the drawings, it will be understood that the illustrated user interface text and controls are provided as examples only and are not meant to be limiting. Other suitable user interface elements may be possible.

We claim:

1. A system for curating medical images for a medical image database, the system comprising: a communication component to provide access to the one or more images via a network; and a processor in communication with the communication component, the processor being operable to: obtain one or more query medical images, each query medical image having an identifier that is representative of image data of that query medical image; assign each query medical image to at least one initial set of related medical images from the medical image database based on the identifier for that query medical image, the initial set comprising the query medical image and at least one supplemental medical image; and for each initial set of related medical images, generate a similarity indicator for each medical image of the initial set, the similarity indicator representing a measure of similarity between image data of that medical image and image data of the initial set; and define an intermediate set of medical images from the initial set based on the similarity indicator of each medical image of the initial set; and for each intermediate set of related medical images, generate a relevancy indicator for each medical image of the intermediate set, the relevancy indicator being representative of a measure of the relevancy between the medical image and the intermediate set, the relevancy being representative of correlations between a plurality of relevance parameters associated with the medical image and the intermediate set; and define a curated set of medical images for storage in the medical image database from the medical images in the intermediate set based on the relevancy indicator of each medical image, wherein
the processor is operable to, for each intermediate set: receive the plurality of relevance parameters for each of the medical images of the intermediate set; generate a plurality of membership values by applying a set of input membership functions to the relevance parameters for each medical image of the intermediate set; generate an output membership function for each medical image of the intermediate set by applying a set of rules to the plurality of membership values for that medical image of the intermediate set to quantify the relevancy of that medical image of the intermediate set; and generate the relevancy indicator for each of the medical images of the intermediate set by quantifying the output membership function for that medical image.

2. The system of claim 1, wherein the curated set of medical images excludes the query medical image.

3. The system of claim 1, wherein the curated set of medical images comprises the query medical image.

4. The system of claim 3, wherein the curated set of medical images excludes one or more supplemental medical images.

5. The system of claim 1, wherein the processor is operable to for each medical image of the intermediate set, normalize a measure of relevancy between relevance parameters of the query medical image and relevance parameters of medical images of the intermediate set of medical images.

6. The system of claim 1, wherein the processor is operable to:
determine whether the relevancy indicator for a medical image exceeds a first relevancy threshold; and
in response to determining that the relevancy indicator of the medical image does not exceed the first relevancy threshold, exclude the medical image from the curated set of medical images, otherwise assign the medical image to the curated set of medical images.

7. The system of claim 1, wherein the processor is operable to store a version of a medical image in the curated set of medical images.

8. The system of claim 7, wherein the processor is operable to, for each of the one or more versions of a medical images:
identify one or more portions of image data of the version of the medical image that is analogous to image data of the another medical image in the curated set of medical images; and
store the one or more portions of image data of the medical image that is analogous to image data of the other medical image in the curated set; and
store a remaining portion of image data of the version of the medical image that is not analogous to other medical images in the curated set of medical images.

9. The system of claim 8, wherein the remaining portion of image data comprises low resolution image data.

10. The system of claim 8, wherein the processor is operable to store an association between the analogous image data of the version of the medical image and the other medical image in the curated set.

11. The system of claim 8, wherein the processor is operable to store higher resolution image data of the one or more portions of analogous image data from the version of the medical image.

12. The system of claim 8, wherein the one or more portions of image data of the medical images in the curated set are sorted in order of similarity to the version of the medical image.

13. The system of claim 12 wherein the one or more portions of image data of the medical images in the curated set are sorted in order of decreasing similarity to the version of the medical image.

14. The system of claim 12, wherein the processor is operable to determine a measure of similarity between the identifier of the version of the medical image and identifiers for the other medical images in the curated set of medical images.

15. The system of claim 1, wherein the processor is operable to:
   determine whether the relevancy indicator of a medical image exceeds a second relevancy threshold; and
   in response to determining that the relevancy indicator of the medical image does not exceed the second relevancy threshold, store a version of a medical image in the curated set of medical images, otherwise store the medical image in the curated set of medical images.

16. The system of claim 1, wherein the processor is operable to generate the identifier for the query medical image.

17. The system of claim 1, wherein the processor is operable to store the identifier for the query medical image in the medical image database.

18. The system of claim 1, wherein the processor is operable to store the relevancy indicator for the query medical image in the medical image database.

19. The system of claim 1, wherein the processor is operable to, for each supplemental medical image of the initial set, normalize a measure of similarity between the identifier of the query medical image and the identifier of the supplemental medical image.

20. The system of claim 1, wherein the processor is operable to:
   determine whether the similarity indicator for that medical image exceeds a similarity threshold; and
   in response to determining that the similarity indicator for that medical image exceeds the similarity threshold, assign that medical image to the intermediate set.

21. The system of claim 20, wherein the processor is operable to temporarily store the query medical images.

22. The system of claim 20, wherein the processor is operable to delete the query medical images.

23. The system of claim 20, wherein the processor is operable to store the similarity indicator for the query medical image in the medical image database.

24. The system of claim 1, wherein the processor is operable to:
   obtain the one or more query medical images from an imaging device; and
   for each query medical image, generate the identifier that is representative of image data of that query medical image.

* * * * *

UNITED STATES PATENT AND TRADEMARK OFFICE
CERTIFICATE OF CORRECTION

PATENT NO. : 11,615,895 B2
APPLICATION NO. : 17/901098
DATED : March 28, 2023
INVENTOR(S) : Hamid Reza Tizhoosh, Patrick Myles and Savvas Damaskinos It is certified that error appears in the above-identified patent and that said Letters Patent is hereby corrected as shown below:

In the Specification

Column 32, Line 36:
"8141"
Should read:
-- 8141 --

Column 32, Line 61:
"8241"
Should read:
-- 8241 --

Column 32, Line 63:
"8241"
Should read:
-- 8241 --

Column 32, Line 66:
"8241"
Should read:
-- 8241 --

Column 32, Line 67:
"8141"
Should read:
-- 8141 --

Signed and Sealed this
Twenty-seventh Day of August, 2024

Katherine Kelly Vidal
*Director of the United States Patent and Trademark Office*

CERTIFICATE OF CORRECTION (continued)
U.S. Pat. No. 11,615,895 B2

Column 33, Line 1:
"8141"
Should read:
-- 814l --

Column 33, Line 2:
"8241"
Should read:
-- 824l --

Column 33, Line 3:
"8241"
Should read:
-- 824l --

Column 33, Line 4:
"8141"
Should read:
-- 814l --

Column 33, Line 28:
"8241"
Should read:
-- 824l --